United States Patent
Hane

(10) Patent No.: US 12,299,922 B2
(45) Date of Patent: May 13, 2025

(54) LUMINAL STRUCTURE CALCULATION APPARATUS, CREATION METHOD FOR LUMINAL STRUCTURE INFORMATION, AND NON-TRANSITORY RECORDING MEDIUM RECORDING LUMINAL STRUCTURE INFORMATION CREATION PROGRAM

(71) Applicant: OLYMPUS CORPORATION, Tokyo (JP)

(72) Inventor: Jun Hane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 381 days.

(21) Appl. No.: 17/888,907

(22) Filed: Aug. 16, 2022

(65) Prior Publication Data
US 2022/0398771 A1 Dec. 15, 2022

Related U.S. Application Data

(63) Continuation of application No. PCT/JP2020/006444, filed on Feb. 19, 2020.

(51) Int. Cl.
*A61B 34/20* (2016.01)
*A61B 1/06* (2006.01)
(Continued)

(52) U.S. Cl.
CPC .............. *G06T 7/73* (2017.01); *A61B 1/06* (2013.01); *G06T 7/55* (2017.01); *G06T 2207/10068* (2013.01); *G06T 2207/30028* (2013.01)

(58) Field of Classification Search
CPC ... G06T 7/73; G06T 7/55; G06T 2207/10068; G06T 2207/30028; G06T 7/579;
(Continued)

(56) References Cited

U.S. PATENT DOCUMENTS 9,129,435 B2 * 9/2015 Lee ................... G06T 3/4038
9,454,711 B2 * 9/2016 Mitsui ................ G06V 10/811
(Continued)

FOREIGN PATENT DOCUMENTS

EP  2 082 678 A1  7/2009
EP  2 213 220 A1  8/2010
(Continued)

OTHER PUBLICATIONS

International Search Report dated Apr. 21, 2020 received in PCT/JP2020/006444.
(Continued)

*Primary Examiner* — Bobbak Safaipour
*Assistant Examiner* — Joshua Chen
(74) *Attorney, Agent, or Firm* — Scully, Scott, Murphy & Presser, P.C.

(57) ABSTRACT

A luminal structure calculation apparatus includes at least one processor including hardware. The processor acquires picked-up images at a plurality of points in time including a same site of an object acquired by an image pickup unit provided in an insertion section inserted into a lumen serving as the object and three-dimensional disposition including information concerning at least a part of a position or a direction of the image pickup unit and calculates a position of the same site based on the picked-up images at the plurality of points in time and the three-dimensional disposition to calculate a three-dimensional structure of the lumen.

13 Claims, 19 Drawing Sheets

(51) Int. Cl.
*A61B 1/31* (2006.01)
*G06T 7/55* (2017.01)
*G06T 7/60* (2017.01)
*G06T 7/73* (2017.01)

(58) Field of Classification Search
CPC ............ G06T 2207/10016; A61B 1/06; A61B 90/361; A61B 2034/105; A61B 2034/2051; A61B 2034/2059; A61B 2034/2061; A61B 2090/371; A61B 1/00194

See application file for complete search history.

(56) References Cited

U.S. PATENT DOCUMENTS

| | | | |
|---|---|---|---|
| 9,892,516 B2* | 2/2018 | Moteki | G06T 7/579 |
| 10,140,733 B1* | 11/2018 | Liu | G06V 10/46 |
| 2009/0221869 A1 | 9/2009 | Tanaka | |
| 2010/0204547 A1 | 8/2010 | Tanaka et al. | |
| 2012/0287238 A1* | 11/2012 | Onishi | A61B 1/0005 348/45 |
| 2017/0112578 A1* | 4/2017 | Ikuma | A61B 1/05 |
| 2020/0060528 A1 | 2/2020 | Akimoto | |
| 2022/0198742 A1* | 6/2022 | Nishide | G06V 10/82 |

FOREIGN PATENT DOCUMENTS

| | | | | |
|---|---|---|---|---|
| JP | 2006-288752 A | | 10/2006 | |
| JP | 6422321 B2 | * | 11/2018 | |
| JP | 2019028610 A | * | 2/2019 | |
| WO | 2008/059636 A1 | | 5/2008 | |
| WO | 2009/069395 A1 | | 6/2009 | |
| WO | WO-2017212725 A1 | * | 12/2017 | ............... A61B 1/00 |
| WO | 2018/230098 A1 | | 12/2018 | |
| WO | WO-2019202827 A1 | * | 10/2019 | |

OTHER PUBLICATIONS

Mohammad Ali Armin, et al. "Automated visibility map of the internal colon surface from colonoscopy video", International Journal of Computer Assisted Radiology and Survey, vol. 11, No. 9, p. 1599 to 1610, Aug. 4, 2016.

DongHo Hong, "3D Colon Segment and Endoscopy Motion Reconstruction from Colonoscopy Video", Iowa State University, 2012.

* cited by examiner

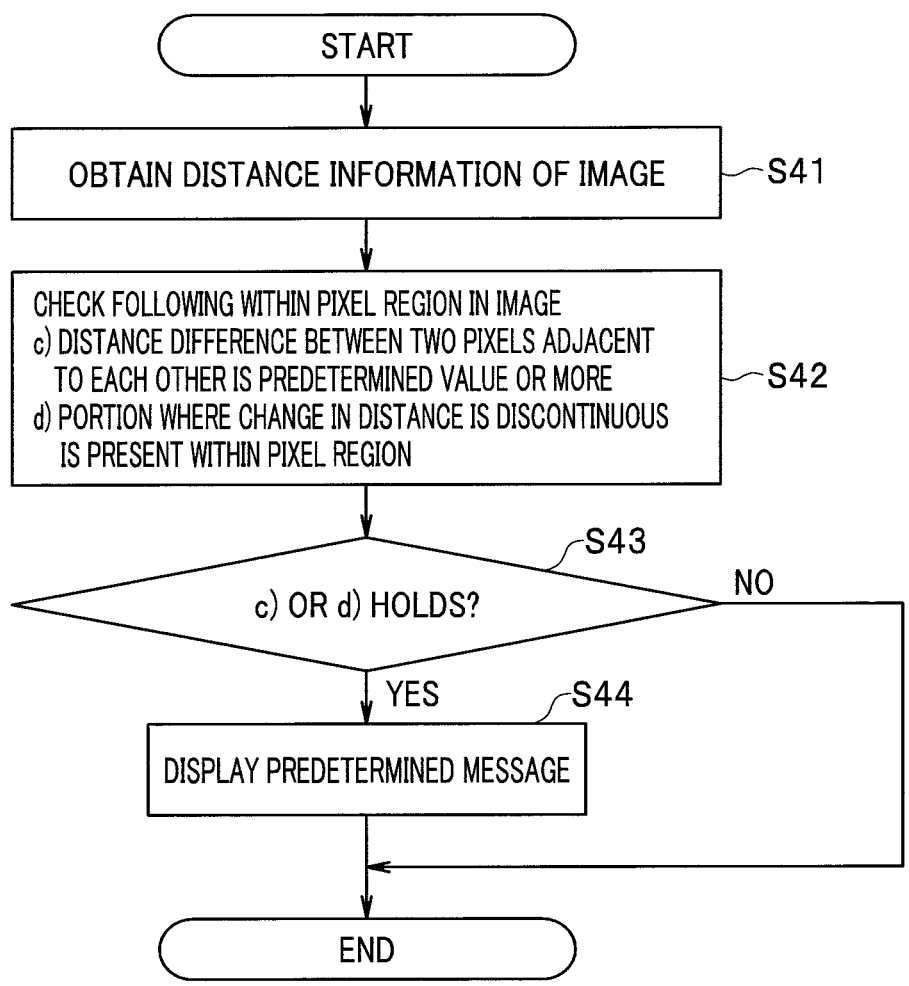

LUMINAL STRUCTURE CALCULATION APPARATUS, CREATION METHOD FOR LUMINAL STRUCTURE INFORMATION, AND NON-TRANSITORY RECORDING MEDIUM RECORDING LUMINAL STRUCTURE INFORMATION CREATION PROGRAM

CROSS REFERENCE TO RELATED APPLICATION

This application is a continuation application of PCT/JP2020/006444 filed on Feb. 19, 2020, the entire contents of which are incorporated herein by this reference.

BACKGROUND OF THE INVENTION

1. Field of the Invention

The present invention relates to a luminal structure calculation apparatus, a creation method for luminal structure information, and a non-transitory recording medium recording a luminal structure information creation program.

2. Description of the Related Art

Endoscopes are widely used in a medical field and an industrial field. For example, in the medical field, a doctor can perform an endoscopic examination or the like by inserting an insertion section of an endoscope into a subject and viewing an endoscopic image displayed on a display apparatus to observe an inside of the subject.

In the endoscopic examination, if an unobserved part is present, a reliable endoscopic examination is not ensured. Therefore, for the purpose of, for example, grasping an unobserved part of a colonoscope, for example, in "Automated visibility map of the internal colon surface from colonoscopy video" by Mohammad Ali Armine and five others (International Journal of Computer Assisted Radiology and Survey, Vol. 11, No. 9, P. 1599 to 1610, 4 Aug. 2016), a technique for constructing a three-dimensional model structure of an intestinal tract with estimation by an arithmetic operation based on an image obtained by being picked up by an endoscope is proposed.

In the proposal, the three-dimensional model structure is calculated only from an endoscopic image. In order to calculate the three-dimensional model structure, coordinates of a plurality of feature points on an inner wall of the intestinal tract in the endoscopic image are calculated and the three-dimensional model structure is created to connect the plurality of feature points.

SUMMARY OF THE INVENTION

A luminal structure calculation apparatus according to an aspect of the present invention includes at least one processor including hardware. The processor acquires picked-up images at a plurality of points in time including a same site of an object acquired by an image sensor provided in an insertion section inserted into a lumen serving as the object and three-dimensional disposition including information concerning at least a part of a position or a direction of the image sensor and calculates a position of the same site based on the picked-up images at the plurality of points in time and the three-dimensional disposition to calculate a three-dimensional structure of the lumen.

A creation method for luminal structure information according to an aspect of the present invention includes: acquiring picked-up images of an object at a plurality of points in time including a same site of the object acquired by an image sensor provided in an insertion section inserted into a lumen serving as the object; acquiring three-dimensional disposition including information concerning at least one of a position or a direction of the insertion section; and calculating a position of the same site based on the picked-up images at the plurality of points in time and the three-dimensional disposition to calculate a three-dimensional structure of the lumen.

In a non-transitory recording medium recording a luminal structure information creation program according to an aspect of the present invention, the luminal structure information creation program causes a computer to execute: processing for acquiring picked-up images of an object at a plurality of points in time including a same site of the object acquired by an image sensor provided in an insertion section inserted into a lumen serving as the object; processing for detecting three-dimensional disposition including information concerning at least one of a position or a direction of the insertion section; and processing for calculating a position of the same site based on the picked-up images at the plurality of points in time and the three-dimensional disposition to calculate a three-dimensional structure of the lumen.

BRIEF DESCRIPTION OF THE DRAWINGS

FIG. 25 is a flowchart showing an example of a flow of notification processing for an unobserved region by a distance image of the distance sensor according to the embodiment of the present invention.

DETAILED DESCRIPTION OF THE PREFERRED EMBODIMENT

In general, since an organ such as a large intestine has mobility, if an image failure due to a movement or the like of the organ occurs while a three-dimensional model structure is created, positions of feature points are unclear and a three-dimensional model structure connecting a plurality of points cannot be calculated.

Therefore, according to an embodiment of the present invention, it is possible to provide a luminal structure calculation apparatus, a creation method for luminal structure information, and a non-transitory recording medium recording a luminal structure information creation program capable of calculating a three-dimensional model structure of a lumen from positions of respective feature points even if an image failure due to a movement or the like of an organ occurs.

An embodiment of the present invention is explained below with reference to the drawings.
(Configuration)

Figure 1:
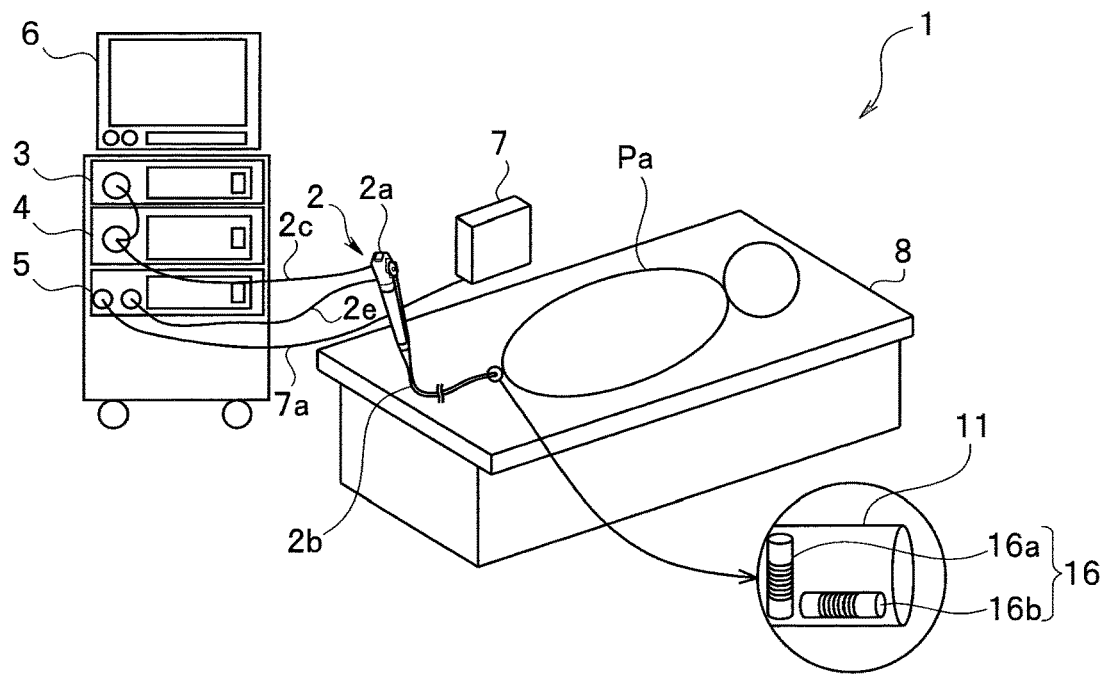
FIG. 1 is a configuration diagram of an endoscope system according to an embodiment of the present invention.
Figure 2:
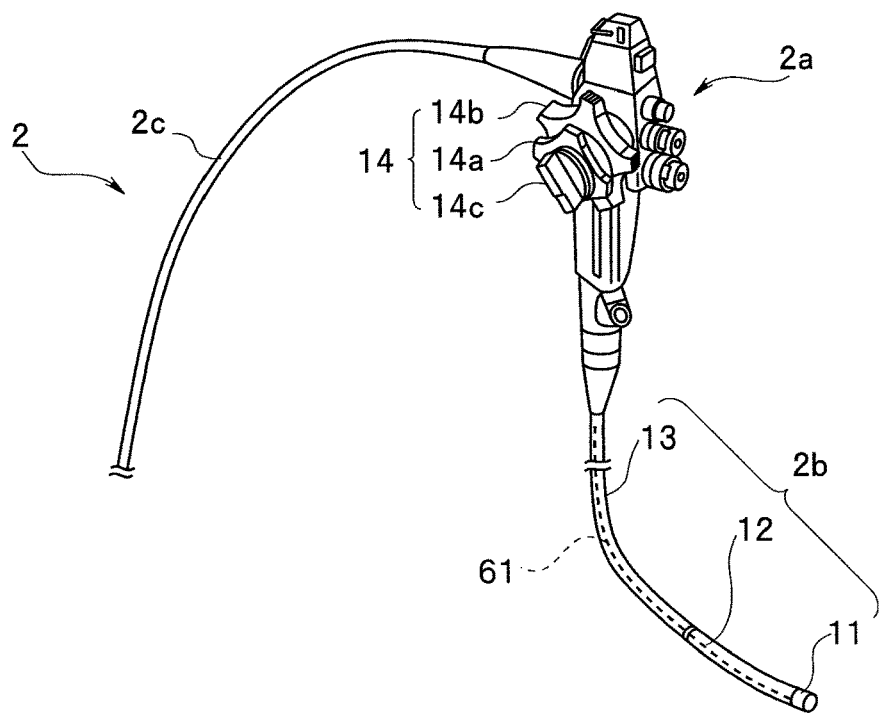
FIG. 2 is a perspective view of an endoscope according to the embodiment of the present invention.
Figure 3:
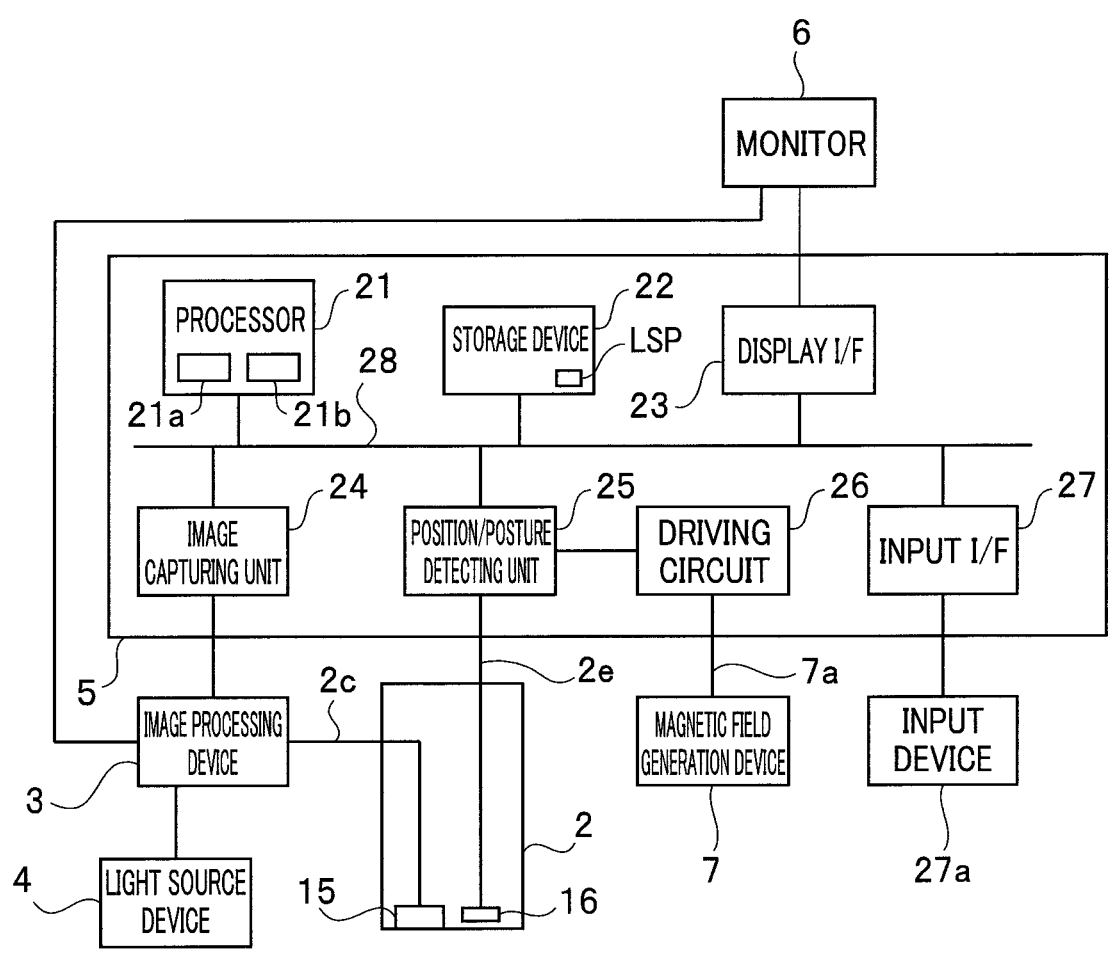
FIG. 3 is a block diagram showing a configuration of the endoscope system according to the embodiment of the present invention.

FIG. 1 is a configuration diagram of an endoscope system according to the present embodiment. FIG. 2 is a perspective view of an endoscope. FIG. 3 is a block diagram showing a configuration of an endoscope system 1. The endoscope system 1 includes an endoscope 2, an image processing apparatus 3, a light source apparatus 4, a luminal structure detection apparatus 5, a monitor 6, which is a display apparatus, and a magnetic field generation apparatus 7. The endoscope system 1 is capable of performing normal light observation performed using white illumination light. A doctor can perform, using the endoscope system 1, an endoscopic examination of an inside of a large intestine of a patient Pa lying to face upwards on a bed 8. The luminal structure detection apparatus 5 is a luminal structure calculation apparatus that calculates a luminal structure of the large intestine of the patient Pa.

Note that, here, the magnetic field generation apparatus 7 is an independent apparatus but may be included in the luminal structure detection apparatus 5.

The endoscope 2 includes an operation section 2a, an insertion section 2b having flexibility, and a universal cable 2c including a signal line. The endoscope 2 is a tubular insertion apparatus for inserting the insertion section 2b having a tubular shape into a body cavity. A connector is provided at a distal end of the universal cable 2c. The endoscope 2 is detachably connected to the light source apparatus 4 and the image processing apparatus 3 by the connector. Here, the endoscope 2 is an endoscope insertable into the large intestine. Further, although not illustrated, a light guide is inserted through the universal cable 2c. The endoscope 2 is configured to emit illumination light, which is emitted from the light source apparatus 4, from a distal end of the insertion section 2b through the light guide.

As shown in FIG. 2, the insertion section 2b includes a distal end portion 11, a bendable bending section 12, and a flexible tube section 13 from the distal end toward a proximal end of the insertion section 2b. The insertion section 2b is inserted into a lumen of the patient Pa, which is an object. A proximal end portion of the distal end portion 11 is connected to a distal end of the bending section 12. A proximal end portion of the bending section 12 is connected to a distal end of the flexible tube section 13. The distal end portion 11 is a distal end portion of the insertion section 2b, that is, a distal end portion of the endoscope 2 and is a hard distal end rigid portion.

The bending section 12 is capable of bending in a desired direction according to operation on a bending operation member 14 (a left-right bending operation knob 14a and an up-down bending operation knob 14b) provided in the operation section 2a. When the bending section 12 is bent, a position and a direction of the distal end portion 11 are changed, and an observation site in a subject is grasped within an observation visual field, the observation site is irradiated with illumination light. The bending section 12 includes a plurality of bending pieces (not shown) coupled in a longitudinal axis direction of the insertion section 2b. Accordingly, the doctor can thoroughly observe the inside of the large intestine of the patient Pa by bending the bending section 12 in various directions while pushing the insertion section 2b into the large intestine or while pulling the insertion section 2b from the large intestine.

The left-right bending operation knob 14a and the up-down bending operation knob 14b cause an operation wire inserted through the insertion section 2b to be towed and slacked in order to bend the bending section 12. The bending operation member 14 further includes a fixing knob 14c that fixes a position of the bent bending section 12. Note that, besides the bending operation member 14, various operation buttons such as a release button and an air feeding and water feeding button are provided in the operation section 2a.

The flexible tube section 13 has flexibility and bends according to an external force. The flexible tube section 13 is a tubular member extended from the operation section 2a.

As shown in FIG. 3, an image pickup device 15, which is an image pickup apparatus, is provided at the distal end portion 11 of the insertion section 2b. An image of an observation site in the large intestine illuminated by illumination light of the light source apparatus 4 is picked up by the image pickup device 15. In other words, the image pickup device 15 is provided at the distal end portion 11 of the insertion section 2b and configures an image pickup unit that picks up images in the subject at a plurality of points in time and acquires picked-up images at the plurality of points in time. An image pickup signal obtained by the image pickup device 15 is supplied to the image processing apparatus 3 through the signal line in the universal cable 2c.

The image processing apparatus 3 is a video processor that performs predetermined image processing on the received image pickup signal and generates an endoscopic image. A video signal of the generated endoscopic image is outputted from the image processing apparatus 3 to the monitor 6 and a live endoscopic image is displayed on the monitor 6. The doctor, who performs an examination, can insert the distal end portion 11 of the insertion section 2b from an anus of the patient Pa and observe the inside of the large intestine of the patient Pa.

Further, a magnetic sensor 16 is disposed at the distal end portion 11 of the insertion section 2b. More specifically, the magnetic sensor 16 is a detection apparatus disposed near the image pickup device 15 of the distal end portion 11 and used to detect a position and a posture of a visual point of the image pickup device 15. The magnetic sensor 16 includes two coils 16a and 16b. For example, two center axes of the two coils 16a and 16b having a cylindrical shape are orthogonal to each other. Accordingly, the magnetic sensor 16 is a six-axis sensor and detects a position coordinate and a direction (that is, an Eulerian angle) of the distal end portion 11. A signal line 2e of the magnetic sensor 16 extends from the endoscope 2 and is connected to the luminal structure detection apparatus 5.

In other words, the magnetic sensor 16 can be disposed on an inside of the distal end portion 11 of the insertion section 2b as the detection apparatus for detecting the position and the posture of the visual point of the image pickup device 15 and does not affect a size and performance of the endoscope 2 including the insertion section 2b.

The magnetic field generation apparatus 7 generates a predetermined magnetic field. The magnetic sensor 16 detects the magnetic field generated by the magnetic field generation apparatus 7. The magnetic field generation apparatus 7 is connected to the luminal structure detection apparatus 5 by the signal line 2e. A detection signal of the magnetic field is supplied from the endoscope 2 to the luminal structure detection apparatus 5 through the signal line 2e. Note that a magnetic field generation device may be provided at the distal end portion 11 instead of the magnetic sensor 16 and a magnetic sensor may be provided on an outside of the patient Pa instead of the magnetic field generation apparatus 7 to detect a position and a posture of the distal end portion 11. Here, the position and the posture of the distal end portion 11, in other words, a position and a direction of a visual point of an endoscopic image acquired by the image pickup device 15 are detected in real time.

When the doctor presses the release button provided in the operation section 2a, a release button operation signal is inputted to the image processing apparatus 3. An endoscopic image at a time when the release button is pressed is recorded in a not-shown recorder.

As shown in FIG. 3, the luminal structure detection apparatus 5 includes a processor 21, a storage apparatus 22, a display interface (hereinafter abbreviated as display I/F) 23, an image capturing unit 24, a position/posture detecting unit 25, a driving circuit 26, and an input interface (hereinafter abbreviated as input I/F) 27. The processor 21, the storage apparatus 22, the display I/F 23, the image capturing unit 24, the position/posture detecting unit 25, the driving circuit 26, and the input I/F 27 are connected to one another by a bus 28.

The processor 21 is a control unit that includes a central processing unit (hereinafter referred to as CPU) 21a and a memory 21b and controls processing of the respective units in the structure detection apparatus 5. The memory 21b is a storing unit including a ROM, a RAM and the like. Various processing programs executed by the CPU 21a and various data are stored in the ROM. The CPU 21a can read out and execute various programs stored in the ROM and the storage apparatus 22.

A luminal structure calculation program LSP explained below is stored in the storage apparatus 22. The luminal structure calculation program LSP is a software program for calculating a luminal structure from information concerning a position and a posture of the distal end portion 11 and an endoscopic image. The CPU 21a reads out and executes the luminal structure calculation program LSP, whereby the processor 21 configures a luminal structure calculating unit that calculates a three-dimensional structure of the lumen based on a picked-up image obtained by the image pickup device 15 and three-dimensional disposition (that is, a position and a posture) of the image pickup unit detected by the magnetic sensor 16.

Information concerning a calculated luminal structure and the like are also stored in the storage apparatus 22. The luminal structure information stored in the storage apparatus 22 is outputted through the display I/F 23 and displayed on a screen of the monitor 6. Here, the lumen is a large intestine and a luminal structure image of the large intestine is displayed on the monitor 6.

The monitor 6 has a PinP (picture in picture) function and can display a live endoscopic image obtained by picking up an image with the image pickup device 15 of the endoscope 2 together with a luminal structure image of the large intestine generated by the CPU 21a.

The image capturing unit 24 is a processing unit that captures, at a constant period, an endoscopic image obtained in the image processing apparatus 3. For example, the image capturing unit 24 acquires, from the image processing apparatus 3, thirty endoscopic images in one second, which is the same as a frame rate from the endoscope 2. Note that, here, the image capturing unit 24 captures the thirty endoscopic images in one second. However, the image capturing unit 24 may acquire endoscopic images at a longer period such as three endoscopic images in one second.

The position/posture detecting unit 25 controls the driving circuit 26, which drives the magnetic field generation apparatus 7, and causes the magnetic field generation apparatus 7 to generate a predetermined magnetic field. The position/posture detecting unit 25 detects the magnetic field with the magnetic sensor 16 and generates, from a detection signal of the detected magnetic field, data of a position coordinate (x, y, z) and a direction (that is, an Eulerian angle ($\psi$, $\theta$, $\varphi$)) of the image pickup device 15, that is, information concerning a position and a posture of the image pickup device 15 in real time. In other words, the position/posture detecting unit 25 is a detection apparatus that detects, based on a detection signal from the magnetic sensor 16, three-dimensional disposition including information concerning at least a part of a position or a direction of the image pickup device 15. More specifically, the position/posture detecting unit 25 detects three-dimensional disposition temporal change information, which is information concerning a change in the three-dimensional disposition involved in elapse of time. Accordingly, the position/posture detecting unit 25 acquires three-dimensional disposition information of the insertion section 2b at a plurality of points in time.

An input apparatus 27a such as a mouse and a keyboard is connected to the luminal structure detection apparatus 5. An operation signal corresponding to operation on the input apparatus 27a is inputted to the processor 21 through the input I/F 27.

The light source apparatus 4 is a light source apparatus capable of emitting normal light for a normal light observation mode. Note that, when the endoscope system 1 has a special light observation mode other than the normal light observation mode, the light source apparatus 4 selectively emits the normal light for the normal light observation mode and special light for the special light observation mode. The light source apparatus 4 emits the normal light or the special light as illumination light according to a state of a change-over switch (not shown) for switching an observation mode provided in the image processing apparatus 3.

(Calculation of a Luminal Structure)

Figure 4:
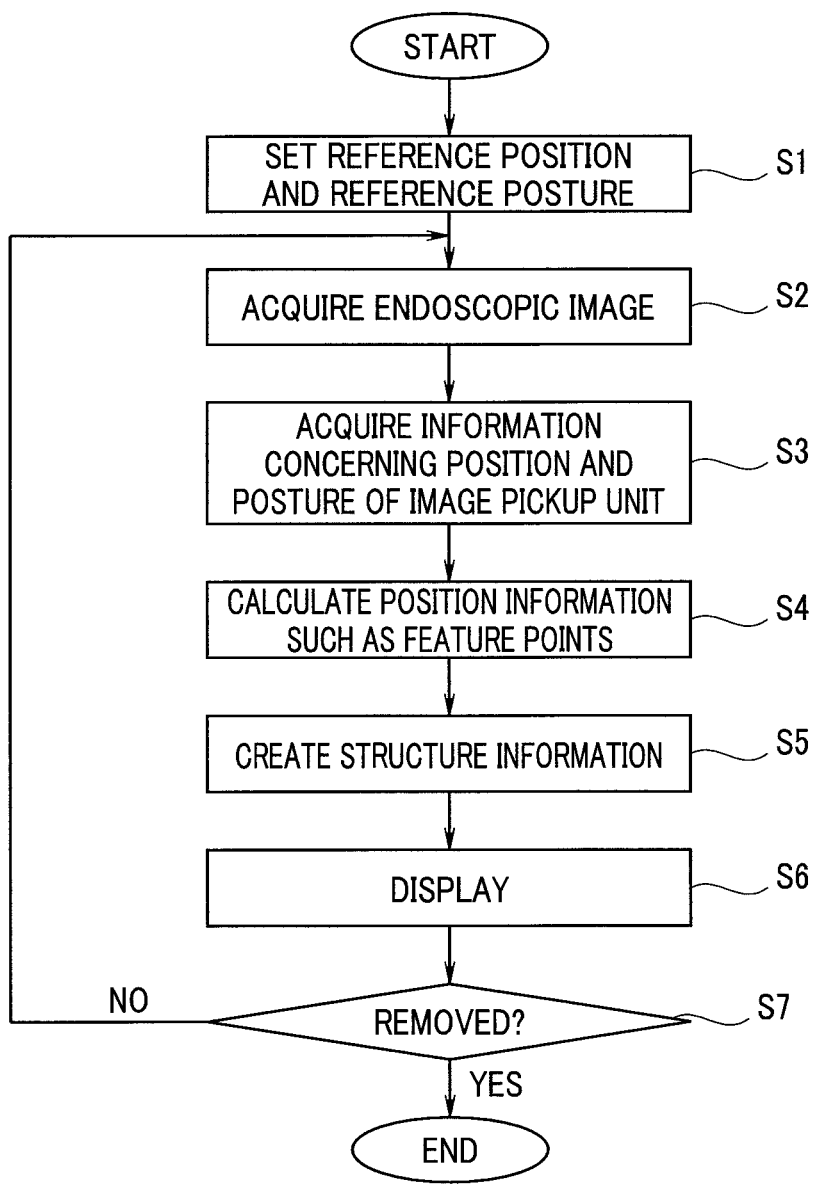
FIG. 4 is a flowchart showing an example of a flow of calculation processing for a luminal structure of a luminal structure calculation program according to the embodiment of the present invention.

FIG. 4 is a flowchart showing an example of a flow of calculation processing for a luminal structure of the luminal structure calculation program LSP. When the doctor presses a predetermined operation button of the input apparatus 27a, the luminal structure calculation program LSP is executed.

Figure 5:
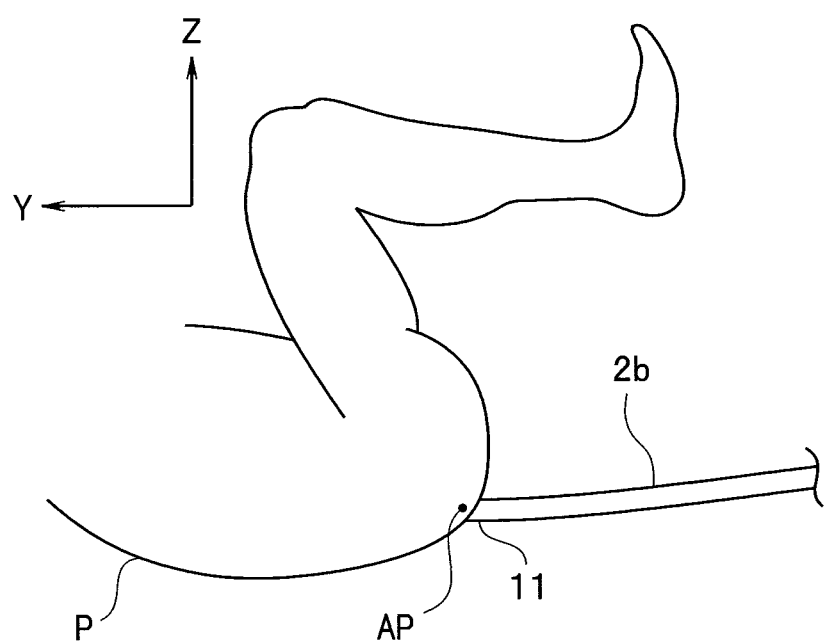
FIG. 5 is a diagram for explaining a state of a patient at a time when an initial value of a distal end portion of an insertion section is set according to the embodiment of the present invention.

First, when the doctor performs predetermined operation on the input apparatus 27a in a state in which the distal end portion 11 of the insertion section 2b is disposed in a position of an anus, the processor 21 sets, as a reference position and a reference posture of the distal end portion 11 in calculating a luminal structure, data of a position (a coordinate) and a posture obtained from the position/posture detecting unit 25 (step (hereinafter abbreviated as S) 1). FIG. 5 is a diagram for explaining a state of the patient Pa at a time when an initial value of the distal end portion 11 is set. As shown in FIG. 5, the doctor sets the reference position and the reference posture of the distal end portion 11 in a position AP of the anus in a three-dimensional space as initial values in a state in which the distal end portion 11 is placed on the anus.

A luminal structure calculated by the following processing is calculated based on the reference position and the reference posture set here.

Note that, after the setting of the reference position and the reference posture, the doctor inserts the distal end portion 11 to a deepest part of the large intestine. In a state in which the distal end portion 11 of the insertion section 2b is present in the deepest part of the large intestine, while feeding air to expand the inside of the large intestine, the doctor moves the insertion section 2b while pulling the insertion section 2b and bends the bending section 12 in various directions and observes an inner wall of the large intestine while stopping pulling out the insertion section 2b halfway. When the doctor is observing the inner wall of the large intestine, a luminal structure of the large intestine is calculated.

As explained above, the image capturing unit 24 acquires an endoscopic image at every predetermined period $\Delta t$ from endoscopic images supplied at every 1/30 second from the image processing apparatus 3 (S2). The period $\Delta t$ is, for example, 0.5 second. The CPU 21a acquires information concerning a position and a posture of the distal end portion 11 outputted by the position/posture detecting unit 25 when the endoscopic image is acquired (S3).

The CPU 21a calculates position information in a three-dimensional space of a plurality of feature points and the like in one endoscopic image acquired in S2 and one or more endoscopic images acquired before the one endoscopic image (S4). A set of the calculated position information of the plurality of feature points and the like is information concerning a luminal structure. As explained below, the position information of the respective feature points may be calculated from image information using a method such as an SLAM (simultaneous localization and mapping) or an SfM (structure from motion) or may be calculated using a principle of triangulation. A calculation method for positions of the respective feature points is explained below.

Note that, when first one endoscopic image is acquired, there is no endoscopic image acquired before the one endoscopic image. Therefore, processing in S4 is not executed until a predetermined number of endoscopic images are acquired.

Positions in the three-dimensional space of the respective feature points are calculated from one group of, that is, one set of feature points and the position and the posture of the image pickup unit and a part of a luminal structure is constructed from the one set of feature points and the like. However, since the large intestine extends and contracts, it is determined, for example, 1) whether calculated two sets of feature points correspond to each other and 2) whether calculated feature points are points corresponding to feature points, positions of which are already calculated. For example, in the case of the determination of 1), a relative movable range of calculated one set of feature points with respect to another one set of feature points is specified by extension and contraction ratios of a large intestine intestinal tract in directions of respective axes of x, y, and z. Accordingly, when two sets of feature points, positions of which are calculated, are not present within a predetermined range determined by a predetermined extension and contraction ratio, the calculated two sets of feature points are not determined the same. In other words, the calculated one set of feature points are not determined the same as the other one set of feature points, the positions of which are already calculated. This means that a part of the feature points of one of the calculated two sets is not included in the feature points of the other of the two sets, the positions of which are already calculated.

A spatial movable range of a calculated feature point is specified by a distance from a fixed portion of the large intestine intestinal tract and the extension and contraction ratio of the large intestine intestinal tract. The fixed portion of the large intestine intestinal tract referred to herein indicates a portion having no mesentery, fixed to a retroperitoneal, and having less mobility such as an anus peripheral portion and portions of an ascending colon and a descending colon of the large intestine. About a feature point, a position of which is already calculated, if a distance from the fixed portion of the large intestine intestinal tract (at least one of an upper end portion of the ascending colon or an upper end portion of the descending colon) is known, when the calculated feature point is not present within a range of a distance obtained by multiplying the distance by a predetermined extension and contraction ratio of an intestinal tract from the fixed portion, the calculated feature point is not determined as the same as the feature point, the position of which is already calculated. This means that a region of the lumen including the feature points and the like of one of the calculated two sets is another portion different from a region of the lumen including the feature points and the like of the other of the two sets, the positions of which are already calculated.

A presence range of an intermediate portion and the like of a sigmoid colon can be checked considering a distance of both sides of an intestinal tract from a fixed portion. A rectum excluding the sigmoid colon and the descending colon are fixed portions. In the intermediate portion of the sigmoid colon, a distance from a connecting portion of the rectum upper end and the sigmoid colon and a distance from an SD junction, which is a connecting portion of the sigmoid colon and the descending colon can be set as two constraint conditions.

Figure 6:
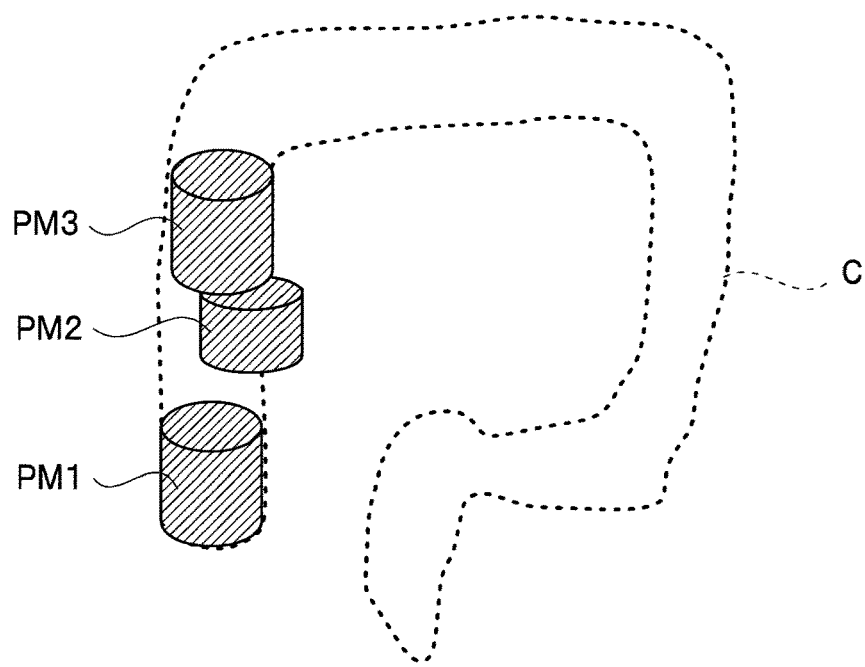
FIG. 6 is a diagram showing an example of a schematic partial model of an inside of a large intestine according to the embodiment of the present invention.

FIG. 6 is a diagram showing an example of a schematic partial model of the inside of the large intestine. According to the determination 1) explained above, one three-dimensional partial model (partial luminal structure) is generated by one set of a feature point group. Therefore, as shown in FIG. 6, positional deviations are present among three three-dimensional partial models PM1, PM2, and PM3 adjacent to one another in an ascending colon of a large intestine intestinal tract C. However, a three-dimensional model of the large intestine including a plurality of three-dimensional partial models PM1, PM2, and PM3 is generated. In other words, the processor 21 functioning as the luminal structure calculating unit calculates a plurality of partial three-dimensional structures, which are parts of a three-dimensional structure, and determines disposition of the plurality of partial three-dimensional structures based on three-dimensional disposition at a time when the respective partial three-dimensional structures are created to calculate a three-dimensional structure of the large intestine intestinal tract C.

Figure 7:
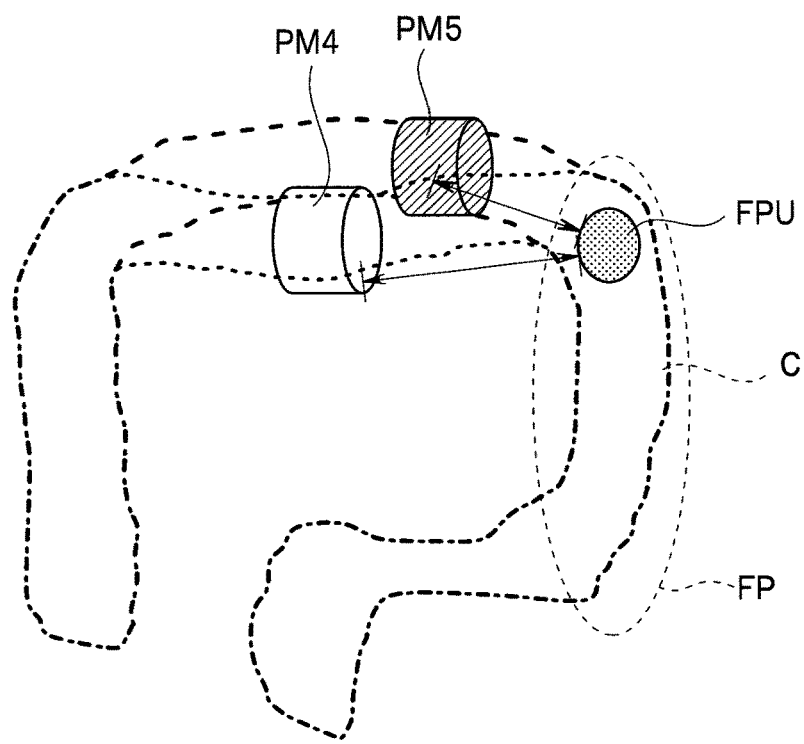
FIG. 7 is a diagram showing an example of a schematic partial model of an inside of the large intestine according to the embodiment of the present invention.

FIG. 7 is a diagram showing an example of a schematic partial model of the inside of the large intestine. If respective feature points of two three-dimensional partial models (partial luminal structures) are present within a range of a distance multiplied by a predetermined extension and contraction ratio from an upper end portion FPU of one fixed portion FP of the large intestine intestinal tract C, the feature points are determined as the same as feature points, positions of which are already calculated. In FIG. 7, distances (distances indicated by arrows in FIG. 7) of respective partial models PM4 and PM5 from the upper end FPU are within the range of the distance multiplied by the predetermined extension and contraction ratio. Since respective feature points of two partial models PM4 and PM5 are present within the range of the distance multiplied by the predetermined extension and contraction ratio from the fixed portion FP of the large intestine intestinal tract, the two partial models PM4 and PM5 are generated as different models and are separated.

Figure 8:
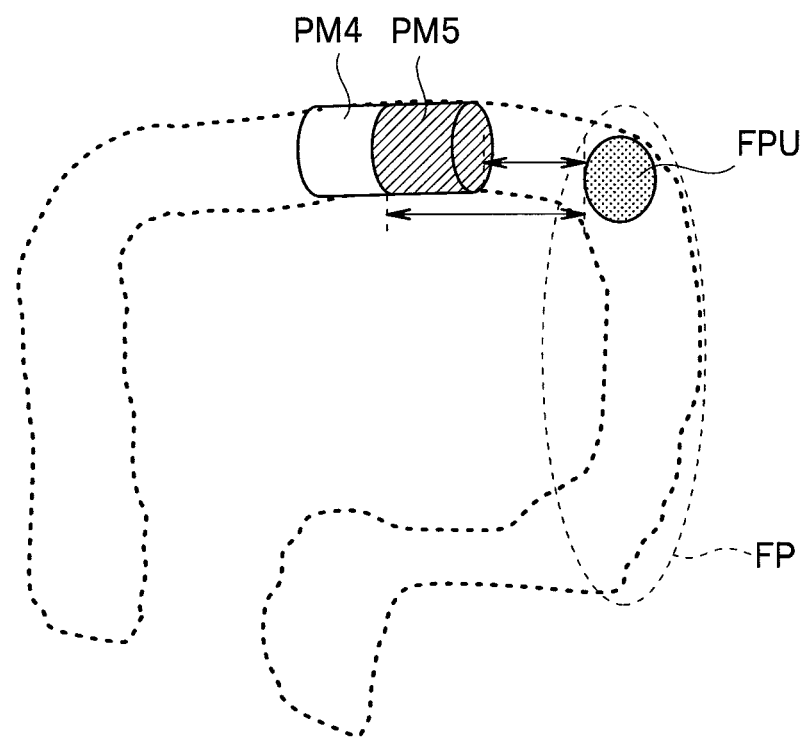
FIG. 8 is a diagram for explaining a method of correcting a positional deviation between two partial models according to the embodiment of the present invention.

Even if the two partial models PM4 and PM5 are separately generated, a positional deviation between the two partial models PM4 and PM5 may be corrected. FIG. 8 is a diagram for explaining a method of correcting the positional deviation between the two partial models PM4 and PM5. The positional deviation of the two partial models PM4 and PM5 having the positional deviation shown in FIG. 7 is corrected as shown in FIG. 8.

Therefore, when similar feature points are extracted among a plurality of three-dimensional structures, the processor 21 compares differences among distances from the similar feature points to the fixed portion with a predetermined reference value to determine whether the similar feature points are feature points common to the plurality of three-dimensional structures.

The partial models PM4 and PM5 are corrected in positions and disposed based on the common feature points such that positions in a lateral direction from the upper end portion FPU of the fixed portion FP coincide. Two distances (distances in a horizontal direction indicated by arrows in FIG. 8) of the partial models PM4 and PM5 from the upper end portion FPU respectively coincide with two distances in the lateral direction (the horizontal direction) of the partial models PM4 and PM5 in FIG. 7.

As explained above, the large intestine intestinal tract C, which is the lumen, includes the fixed portion fixed from the outside and a movable portion (a transverse colon) not fixed from the outside. The processor 21 calculates a distance between a partial three-dimensional structure corresponding to the movable portion and the fixed portion and corrects disposition of the partial three-dimensional structure based on the distance between the partial three-dimensional structure and the fixed portion. The processor 21 calculates a plurality of partial three-dimensional structures including information concerning positions of respective feature points and corrects disposition of the partial three-dimensional models based on positions of feature points common to the plurality of three-dimensional structures.

Therefore, if a part of two sets of feature points coincides as shown in FIG. 8, two partial models adjacent to each other are corrected in positions, whereby it is possible to connect the two adjacent partial models and integrate the two partial models as one model.

Note that the processor 21 can estimate positions of the fixed portion and the movable portion by determining, based on three-dimensional disposition temporal change information, at least one of a turnaround place or a retention place of the insertion section 2b.

A predetermined one extension and contraction ratio may be set for the entire large intestine. However, an extension and contraction ratio of an anus vicinity portion and portions of the ascending colon and the descending colon of the large intestine and an extension and contraction upper limit value of portions other than the anus vicinity portion and the portions of the ascending colon and the descending colon of the large intestine may be set to be different. In other words, a predetermined extension and contraction ratio upper limit value (a threshold) in a three-dimensional space of respective feature points set for each region of the lumen may be used for calculation of positions of the respective feature points. When the positions of the respective feature points are determined, a detected change amount of the positions of the respective feature points is requested to be within a range determined by the extension and contraction ratio upper limit value (the threshold). When the detected change amount of the positions of the feature points is equal to or smaller than the predetermined extension and contraction ratio upper limit value, it is determined that the respective feature points reflected in respective picked-up images are the same.

As explained above, an extension and contraction ratio upper limit value for each region of the lumen including the respective feature points or a change amount upper limit value (a threshold) [0] of the positions of the respective feature points based on a distance from a fixed point of the large intestine intestinal tract and the extension and contraction ratio upper limit value may be considered in calculating the positions of the respective feature points. It is determined, using the predetermined extension and contraction ratio upper limit value of the respective feature points set for each region of the lumen, whether the common feature points reflected in a plurality of picked-up images are the same.

When it is determined by pattern matching that feature points or the like detected at different timings present within the range determined by the extension and contraction ratio coincide, it is determined that these feature points or the like coincide. Information concerning positions set as structure information of the feature points or the like is determined based on information concerning the feature points or the like. For example, as a simple case, information concerning any one of the feature points is adopted as information concerning the positions set as the structure information.

Note that the range determined by the extension and contraction ratio is a range based on the distance from the fixed point of the large intestine intestinal tract of the region of the lumen including the respective feature points and the extension and contraction ratio upper limit value.

The calculated position information of the plurality of feature points or the like is added to structure information data, whereby structure information of the lumen is created (S5). The structure information created in S5 is configured from a set of one or more feature points or the like in a region observed by the endoscope 2.

Figure 9:
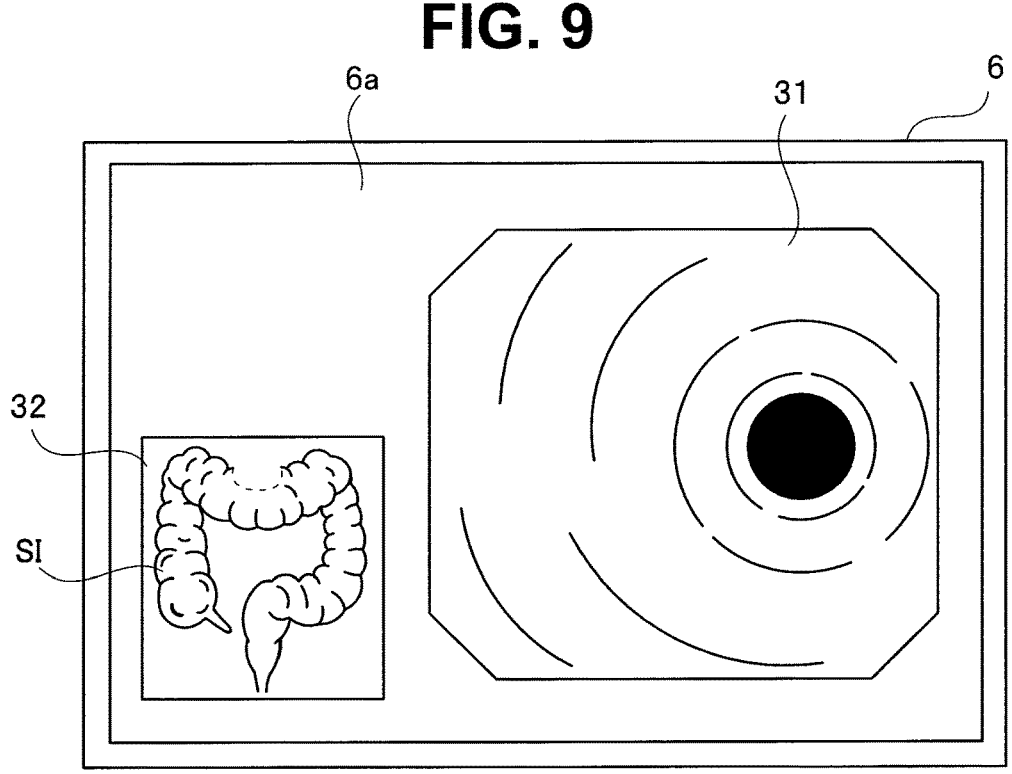
FIG. 9 is a diagram showing an example of an image displayed on a monitor according to an embodiment of the present invention.

The created structure information of the lumen is displayed on the monitor 6 (S6). FIG. 9 is a diagram showing an example of an image displayed on the monitor 6. A display screen 6a of the monitor 6 includes an endoscopic image display region 31 and a structure information display region 32.

Figure 10:
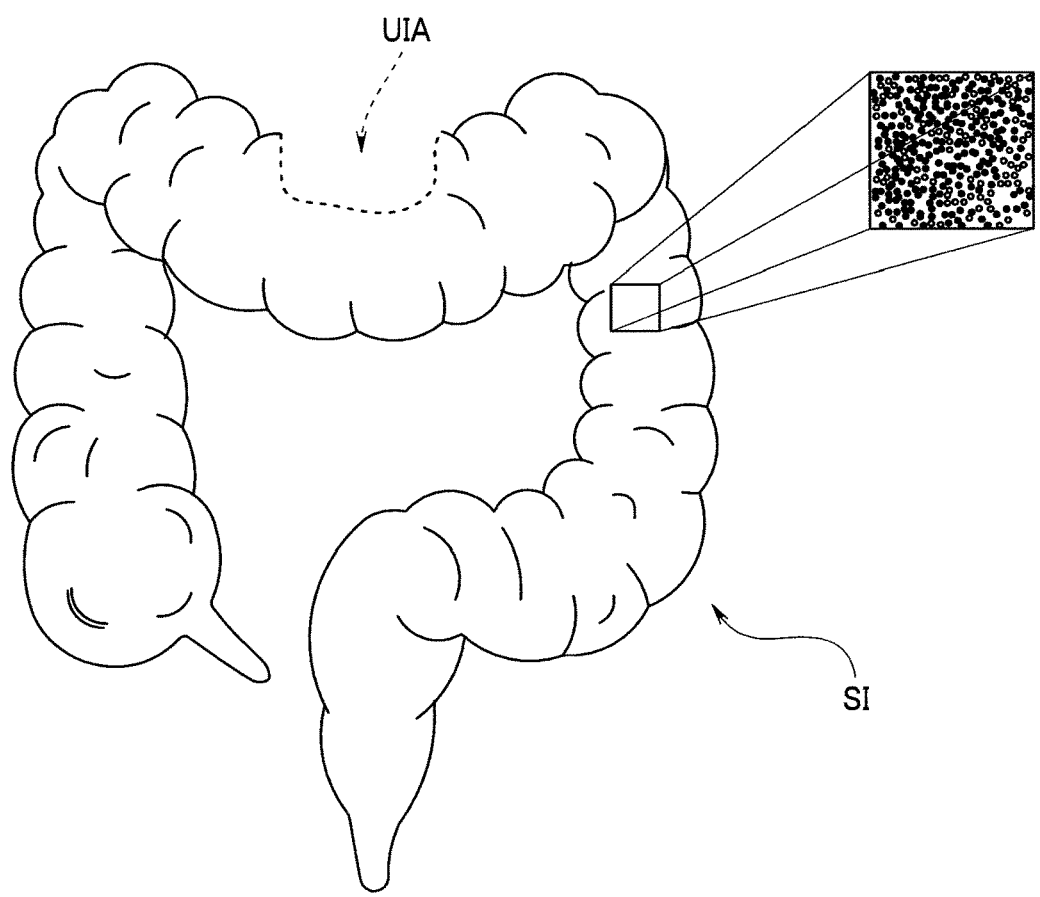
FIG. 10 is a diagram showing an example of an image of structure information displayed in a structure information display region according to the embodiment of the present invention.

The structure information display region 32 is disposed next to the endoscopic image display region 31 for displaying an endoscopic image, which is a live view. Structure information SI generated in S5 is displayed in the structure information display region 32. The structure information SI is an image of a three-dimensional luminal structure of the large intestine viewed from one visual point and is configured from position information of a plurality of feature points or the like. FIG. 10 is a diagram showing an example of an image of the structure information SI displayed in the structure information display region 32. The structure information SI is displayed as a perspective view of the lumen of the large intestine. Since the structure information SI is 3D data, a user, that is, the doctor can check a structure of the lumen viewed from a desired direction in 360 degrees by giving an instruction for changing a visual point position.

As shown in FIG. 10, the structure information SI is a set of the information concerning the feature points or the like calculated in S4. Accordingly, a portion not indicated by the structure information SI means an unobserved part UIA. In FIG. 10, a vicinity of a region indicated by a dotted line is the unobserved part UIA. Accordingly, the doctor can grasp the unobserved part UIA by viewing the luminal structure of the large intestine displayed on the monitor 6.

Figure 11:
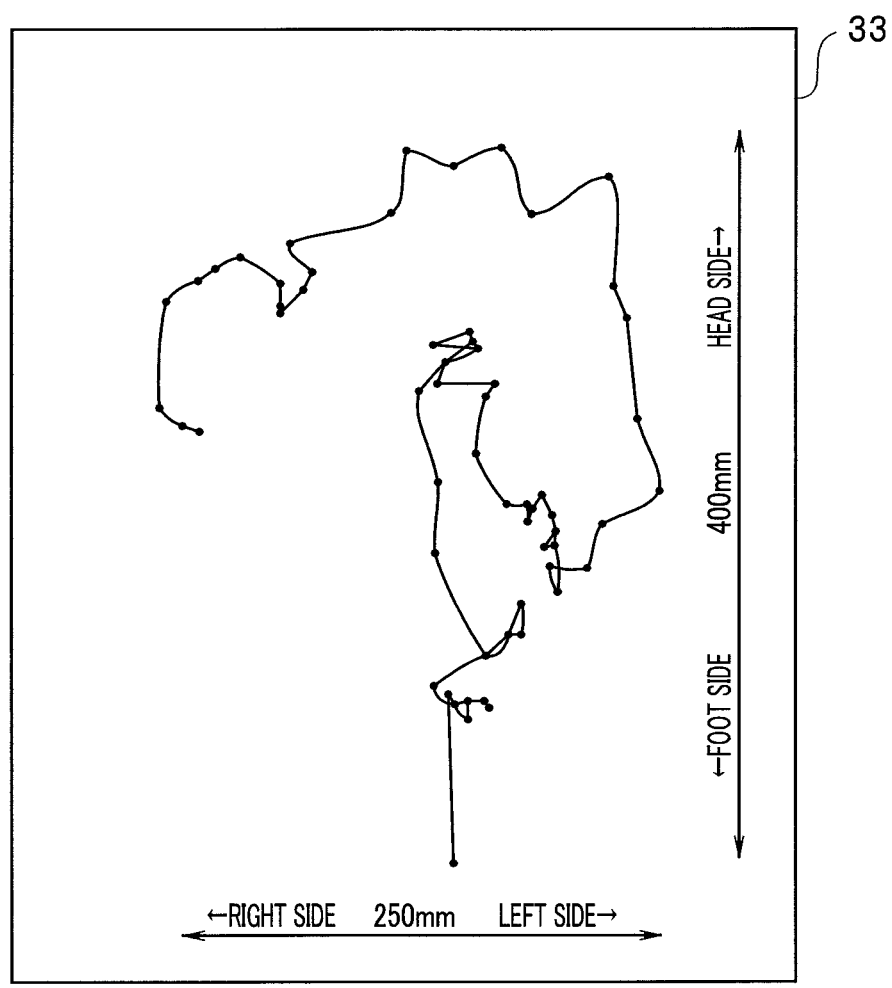
FIG. 11 is a diagram showing an example of an image indicating a trajectory of the distal end portion displayed on the monitor according to the embodiment of the present invention.

The doctor can also operate the input apparatus 27a to supply a predetermined command to the luminal structure detection apparatus 5 and cause the luminal structure detection apparatus 5 to display a time-series movement of the distal end portion 11 from the information concerning the position of the distal end portion 11 acquired in S3. FIG. 11 is a diagram showing an example of an image indicating a trajectory of the distal end portion 11 displayed on the monitor 6. FIG. 11 shows an image of one window 33 displayed on the display screen 6a of the monitor 6. An image indicating a movement in an XY plane of the distal end portion 11 viewed from a Z-axis direction is displayed on the window 33 shown in FIG. 11. In FIG. 11, a predetermined point on the XY plane is set as 0 and the trajectory of the distal end portion 11 is displayed such that a moving distance in X and Y directions is seen in a unit of mm (millimeter). The doctor can grasp the trajectory of the distal end portion 11 by causing the monitor 6 to display the image shown in FIG. 11.

For example, trajectories of the distal end portion 11 of two doctors can be compared based on position information of the distal end portion 11. For example, insertion operation for the insertion section 2b into the large intestine of the same patient Pa can be compared from trajectories of the distal end portion 11 generated from the position information of the distal end portion 11 of the two doctors.

Figure 12:
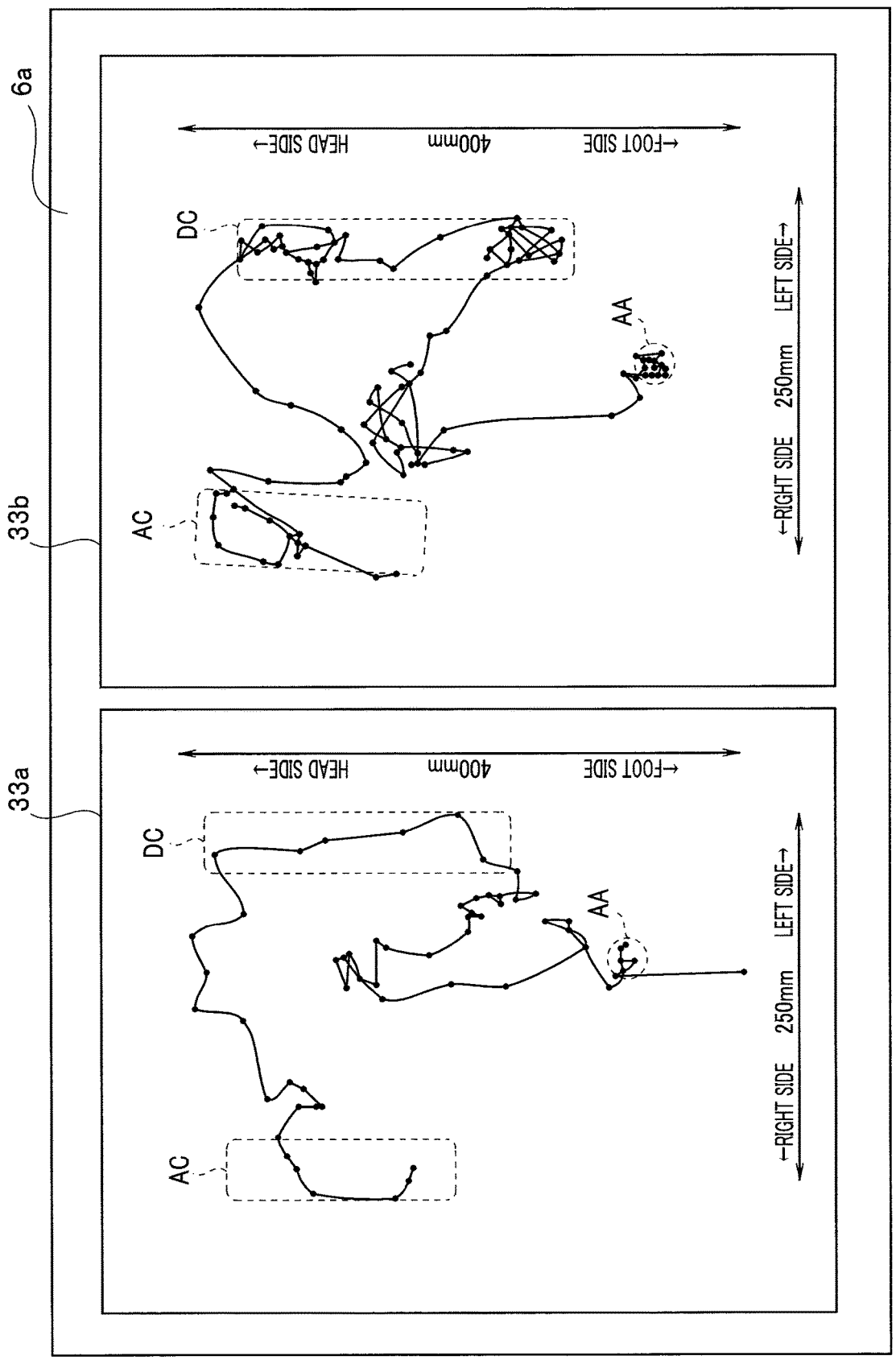
FIG. 12 is a diagram showing a display example at a time when trajectories of the distal end portion of the insertion section about two doctors are displayed on a display screen of the monitor according to the embodiment of the present invention.

FIG. 12 is a diagram showing a display example at a time when, targeting a colon model, trajectories of the distal end portion 11 about the two doctors are displayed on the display screen 6a of the monitor 6. Two windows 33a and 33b are displayed on the display screen 6a. The window 33a displays an image indicating a trajectory of the distal end portion 11 of a doctor A. The window 33b displays an image indicating a trajectory of the distal end portion 11 of a doctor B. The doctor A is an experienced endoscope doctor and the doctor B is a middle standing endoscope doctor.

Compared with the trajectory of the distal end portion 11 of the experienced doctor A displayed on the window 33a, the trajectory of the distal end portion 11 of the middle standing doctor B displayed on the window 33b frequently moves in the vicinity of the anus (AA) in the descending colon (DC) and in the ascending colon (AC) and indicates that the insertion section 2b cannot be smoothly inserted or removed.

Accordingly, it is possible to, for example, compare inserting or removing operation of the insertion section 2b using the trajectory information of the distal end portion 11.
(Calculation of Positions of Feature Points or the Like)

There are various methods for the calculation of the positions of the feature points or the like in S4. Several methods are explained below.
1. When Positions of Feature Points on a Plurality of Continuous Images are Calculated Using a Method Such as the SLAM or the SfM.

A method of performing optimization of bundle adjustment for calculating positions in a three-dimensional space of respective feature points using information concerning a position (a position of the distal end portion 11) and a posture of the image pickup device 15 that picks up an image of an object is explained.

The bundle adjustment is a method of error adjustment for optimizing internal parameters, external parameters, and world coordinate point groups from an image using a nonlinear least square method. For example, world coordinate points of an extracted plurality of feature points are subjected to perspective projection transformation to be transformed into image coordinate points using estimated respective parameters. Respective parameters and respective world coordinate point groups are calculated to minimize a reprojection error.

External parameters about the distal end portion 11 are calculated by solving five-point and eight-point algorithms. Positions of feature points are calculated according to a position of the distal end portion 11 and a triangulation method. An error E between a coordinate of a 3D point projected onto an image plane and feature points by a reprojection error is represented by the following Expression (1).

$$E = \sum_{i=1}^{K} \sum_{j=1}^{L} \|Pi - Psj\|^2 \quad (1)$$

In the expression, L is a number of feature points on K images, Psj is a coordinate position of a 3D point Pi estimated by triangulation and parameters of the distal end portion 11 on the image plane, and Pi is a coordinate position of a corresponding feature point on an image. A position coordinate of the distal end portion 11 is calculated to minimize a function of the error E of Expression (1) using an LM (Levenberg-Marquartdt) method.

The positions in the three-dimensional space of the feature points in S4 explained above are calculated based on coordinate information of extracted feature points on an image and detected information concerning a position and a posture of the distal end portion 11. However, in the present embodiment, the information concerning the position and the posture of the distal end portion 11 is detected by the position/posture detecting unit 25 and is substantially accurate. Accordingly, the information concerning the position and the posture of the distal end portion 11 is not included in estimation targets of the external parameters in the bundle adjustment. Therefore, estimation accuracy of positions in the three-dimensional space of the respective feature points by the bundle adjustment is high and, moreover, a calculation time for positions of an extracted plurality of feature points is short.

Figure 13:
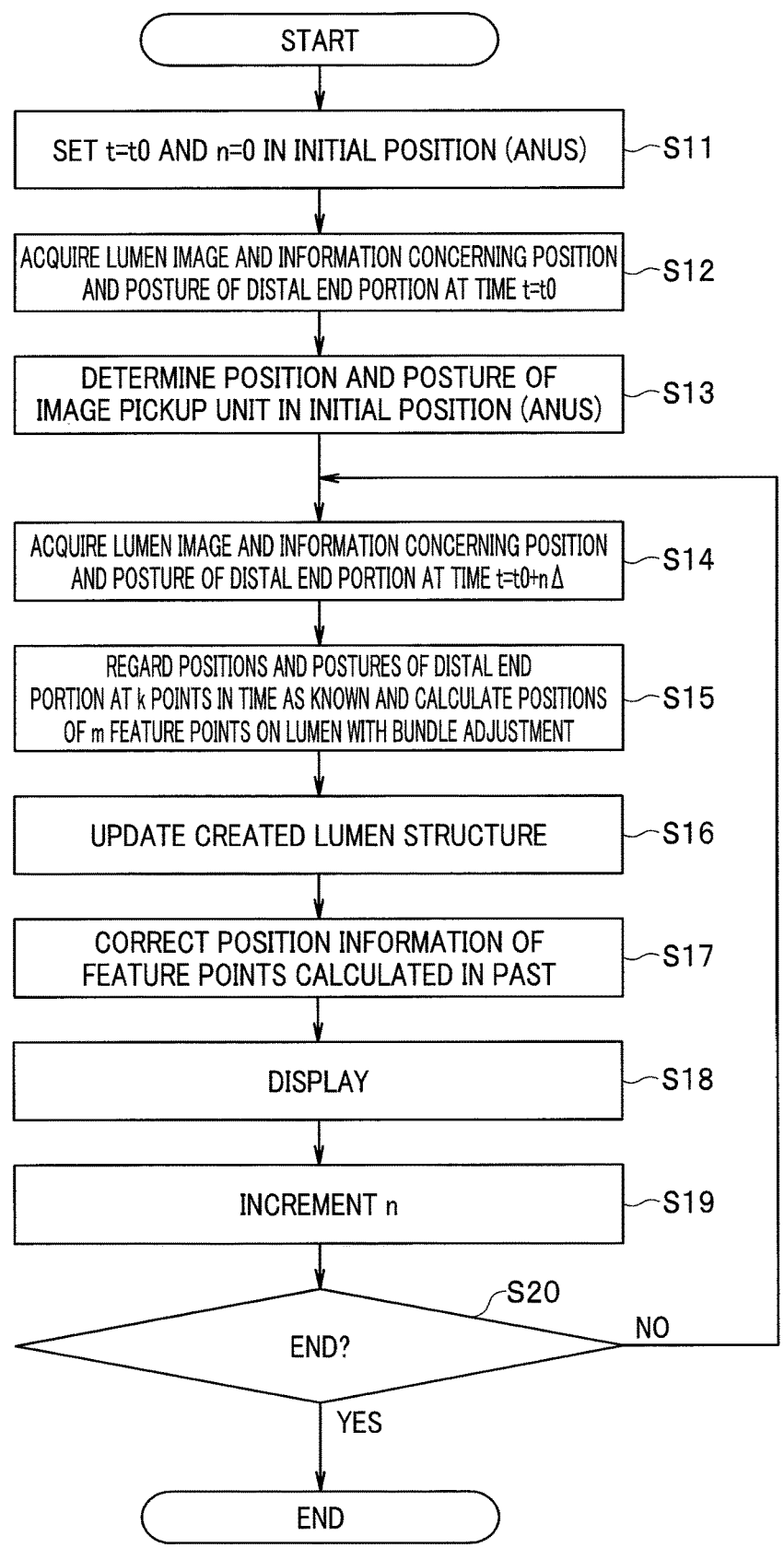
FIG. 13 is a flowchart of a method of performing, with bundle adjustment, position calculation in a three-dimensional space of respective feature points according to the embodiment of the present invention.

FIG. 13 is a flowchart of a method of performing, with the bundle adjustment, the position calculation in the three-dimensional space of the respective feature points.

The processor 21 sets time t when the position AP of the anus shown in FIG. 5 is set as an initial position to t0 and sets a count value n of a software counter to 0 (S11). The processor 21 acquires an endoscopic image (that is, a lumen image) and information concerning a position and a posture of the distal end portion 11 at the time t0 (S12). The endoscopic image is acquired from the image processing apparatus 3. The information concerning the position and the posture of the distal end portion 11 is acquired from the position/posture detecting unit 25.

The processor 21 determines a position and a posture of the distal end portion 11 in the initial position, that is, the position AP of the anus (S13). For example, the position AP of the anus (x, y, z) is determined as (0, 0, 0) and the posture (vx, vy, vz) is determined as (0, 1, 0). S11 and S13 correspond to S1 in FIG. 4.

The processor 21 acquires an endoscopic image and information concerning a position and a posture of the distal end portion 11 at time (t0+nΔt) (S14). S12 and S14 correspond to S2 in FIG. 4.

Note that the information concerning the position and the posture of the distal end portion 11 may be corrected. For example, a path on which the distal end portion 11 passed in the past is corrected using a Kalman filter and a position of the distal end portion 11 in the past is corrected based on the corrected path.

When n reaches k, the processor 21 extracts a plurality of feature points in respective endoscopic images, regards positions and postures of the distal end portion 11, that is, three dimensional disposition at k points in time as known, and calculates, with the bundle adjustment, positions of m feature points included in common in obtained endoscopic images (S15). Accordingly, extraction processing for the plurality of feature points in the respective endoscopic images in S15 configures a feature point extracting unit that extracts a plurality of feature points in respective picked-up images. In S15, feature points reflected in common in picked-up images at a plurality of points in time are extracted. Calculation processing for positions in the three-dimensional space of the respective feature points in S15 configures a three-dimensional position calculating unit that calculates positions in the three-dimensional space of the feature points from positions in the picked-up images of the extracted plurality of feature points and three-dimensional disposition of the insertion section 2b. More specifically, the positions in the three-dimensional space of the feature points are calculated based on three-dimensional disposition information of the insertion section 2b at the plurality of points in time and positions on the picked-up image of the feature points reflected in common in the picked-up images at the plurality of points in time. Positions in the three-dimensional space of the respective feature points are determined by the bundle adjustment.

Figure 14:
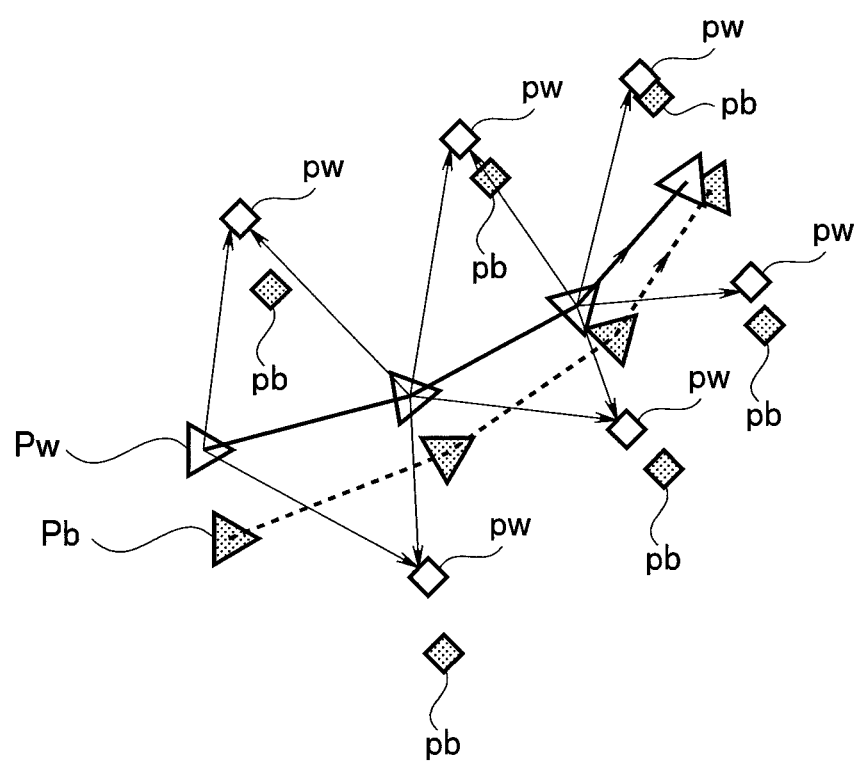
FIG. 14 is a schematic diagram for explaining a relation between feature points on a continuously acquired plurality of endoscopic images and positions and postures of the distal end portion according to the embodiment of the present invention.

FIG. 14 is a schematic diagram for explaining a relation between feature points on a continuously acquired plurality of endoscopic images and positions and postures of the distal end portion 11. In FIG. 14, white triangles Pw indicate actual positions and postures of the distal end portion 11 and black triangles Pb indicate estimated positions and postures of the distal end portion 11. It is indicated that the distal end portion 11 actually moved along a solid line. The estimated distal end portion 11 moves along a dotted line. A position of the distal end portion 11 moves and a posture of the distal end portion 11 changes according to elapse of time.

In FIG. 14, white squares pw indicate actual positions of the feature points and black squares pb indicate estimated, that is, calculated positions of the feature points. The feature points are, for example, parts that are characteristic in shapes and colors in an endoscopic image and are easily discriminated or tracked.

To obtain three-dimensional luminal structure of the large intestine, coordinates of a plurality of specific parts (feature points) on the inner wall of the intestinal tract of the large intestine are calculated and a three-dimensional model is generated by a set of a calculated plurality of coordinates or by joining the coordinates. In other words, a three-dimensional structure of the lumen is determined from the calculated positions of the respective feature points in the three-dimensional space.

As explained above, positions of a certain number or more of feature points on the inner wall of the lumen can be calculated using only the information concerning the endoscopic image. When only the information concerning the endoscopic image is used, the techniques such as the SLAM and the SfM can be used. However, when these techniques are used, coordinates of a plurality of feature points on the inner wall of the intestinal tract are unknown and, in addition, a distal end position and a posture of the endoscope 2 per elapsed time are unknown either. Therefore, an enormous calculation is necessary to estimate positions of the plurality of feature points on the inner wall of the intestinal tract and estimation accuracy is low.

In FIG. 14, since information concerning positions and postures of the image pickup device 15 at respective points in time includes information for six axes, information concerning positions and postures of the image pickup device 15 at k points in time includes 6 k pieces of information. Since the positions of the respective feature points include information for three axes, information concerning positions of m feature points includes 3 m pieces of information. Accordingly, (6 k+3 m) parameters are calculated by an optimization operation of the bundle adjustment.

When a large number of parameters are calculated by the bundle adjustment, since detection errors are accumulated, there is a problem in that a generated three-dimensional model structure deviates. Since a continuous endoscopic image is not obtained because, for example, the distal end portion of the insertion section 2b of the endoscope 2 is pressed against the inner wall of the lumen, there is also a problem in that a three-dimensional model structure cannot be calculated.

In contrast, in the present embodiment, the information concerning the position and the posture of the distal end portion 11 involved in the elapse of time is obtained by the magnetic sensor 16 and regarded as known, it is possible to reduce the number of parameters calculated in the bundle adjustment, reduce a processing amount of the optimization operation, and increase speed of the optimization operation. Further, since positions of feature points can be calculated by the triangulation, a three-dimensional model structure can be calculated even if a continuous endoscopic image is not obtained.

When a position and a posture of the distal end portion 11 and positions in the three-dimensional space of the respective feature points are calculated by the bundle adjustment, there is a problem in that errors of the calculated positions of the respective feature points are accumulated and a luminal structure gradually deviates from an actual structure. However, in the present embodiment, since the position and the posture of the distal end portion 11 are detected by the magnetic sensor 16, such an integration error does not occur.

For example, in the case of FIG. 14 explained above, when the positions of the respective feature points are calculated from only the endoscopic image, the optimization operation for the (6 k+3 m) parameters has been conventionally performed. However, since the information concerning the position and the posture of the distal end portion 11 is known, the optimization operation only calculates 3 m parameters. Therefore, the processing amount of the optimization operation of the bundle adjustment is reduced and the speed of the optimization operation can be increased.

Even when an appropriate continuous endoscopic image is not obtained because, for example, the distal end portion 11 of the insertion section 2b of the endoscope 2 is pressed against the inner wall of the lumen or immersed in dirty cleaning water or an endoscopic image blurs, the information concerning the position and the posture of the distal end portion 11 is obtained. Accordingly, even when a continuous endoscopic image is not obtained because, for example, the distal end portion 11 is pressed against the inner wall of the lumen, possibility that the 3 m parameters can be calculated is increased. As a result, robustness of calculation of a luminal structure is improved.

Referring back to FIG. 13, the processor 21 adds position information of a feature point calculated anew to the created luminal structure information and updates the luminal structure information (S16). S16 corresponds to S5 in FIG. 4.

The processor 21 corrects position information of a feature point calculated in the past (S17). The position information of the feature point calculated in the past among 3 m feature points calculated anew is corrected by, for example, an average operation using position information calculated anew.

Note that processing in S17 does not have to be performed. Position information of respective feature points calculated in the past may be updated by position information of feature points calculated anew.

The processor 21 outputs image data of the luminal structure to the monitor 6 to display an image of the luminal structure in the structure information display region 32 based on the updated luminal structure information (S18). S18 corresponds to S6 in FIG. 4.

After S18, the processor 21 increments n by one (S19) and determines whether an examination end command is inputted (S20). For example, after the insertion section 2b is removed from the large intestine, when the doctor inputs a predetermined command to the input apparatus 27a as the examination end command (S20: YES), the execution of the luminal structure calculation program LSP ends.

When the examination end command is not inputted (S20: NO), the processing shifts to S14. As a result, the processor 21 acquires an endoscopic image later than last acquisition time of an endoscopic image by a period $\Delta t$ (S14) and executes processing in S14 and subsequent steps.

Note that, in the method explained above, the information concerning the position and the posture of the distal end portion 11 is detected by the six-axis magnetic sensor 16 and the three-dimensional positions of the respective feature points are calculated by the optimization of the bundle adjustment. However, a part of all information of the six axes may be regarded as known, that is, at least one of a three-dimensional position (x, y, z) or a three-axis direction (vx, vy, vz) may be regarded as known and the three-dimensional positions of the respective feature points may be calculated by the optimization of the bundle adjustment.

Accordingly, since at least one of the information concerning the position or the posture of the distal end portion 11 is regarded as known and the three-dimensional positions of the respective feature points are calculated in the bundle adjustment, calculation accuracy of the three-dimensional positions of the respective feature points is improved and an overall time of the optimization operation is reduced.

Figure 15:
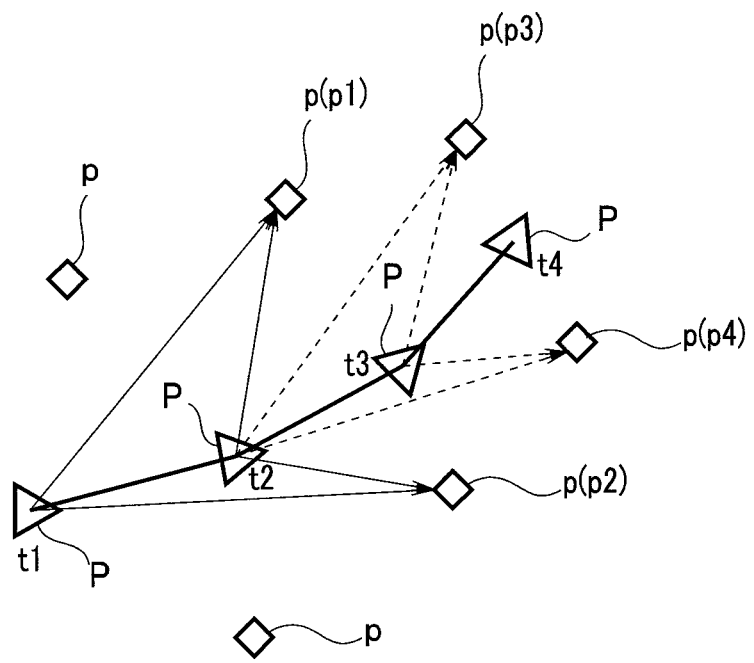
FIG. 15 is a schematic diagram for explaining a relation between feature points on a plurality of endoscopic images and positions and postures of the distal end portion according to the embodiment of the present invention.

2. When a Position of a Feature Point (for Example, a Center Point of an Image) is Calculated from Two Images Using a Triangulation Image A method of calculating positions of respective feature points from two images having different visual points using the triangulation method is explained. FIG. 15 is a schematic diagram for explaining a relation between feature points on a plurality of endoscopic images and positions and postures of the distal end portion 11. In FIG. 15, white triangles P indicate actual positions and postures, that is, three-dimensional disposition of the distal end portion 11. It is indicated that the distal end portion 11 actually moved along a solid line. In FIG. 15, white squares p indicate actual positions of feature points. The respective feature points are, for example, parts that are characteristic in shapes and colors in an endoscopic image and are easily discriminated or tracked.

As indicated by the solid line, positions of feature points p1 and p2 are calculated by the triangulation from information concerning positions and postures of the distal end portion 11 acquired at times t1 and t2 and respective positions of the feature points p1 and p2 on an image acquired at the time t1 and the feature points p1 and p2 on an image acquired at the time t2.

Similarly, as indicated by the dotted line, positions of feature points p3 and p4 are calculated by the triangulation from information concerning positions and postures of the distal end portion 11 acquired at times t2 and t3 and respective positions of the feature points p3 and p4 on an image acquired at the time t2 and the feature points p3 and p4 on an image acquired at the time t4.

As explained above, positions of respective feature points are calculated from information concerning positions and postures of the distal end portion 11 and two endoscopic images using the triangulation. In other words, positions in a three-dimensional space of respective feature points are calculated based on the triangulation from information concerning positions and postures of the image pickup device 15 at a plurality of points in time and positions on picked-up images of feature points reflected in common in picked-up images acquired by the image pickup device 15 at a plurality of points in time and a three-dimensional structure of the lumen is determined.

Note that the triangulation explained above is performed based on two endoscopic images obtained at two points in time but may be performed based on two endoscopic images obtained at the same time.

Figure 16:
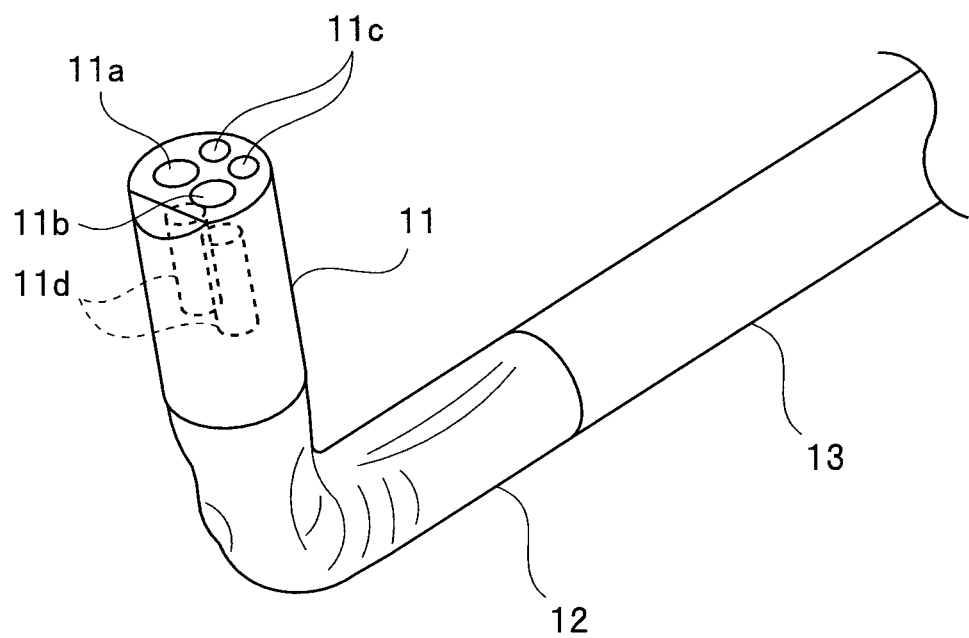
FIG. 16 is a perspective view of a distal end part of the distal end portion of the insertion section including a stereo camera according to the embodiment of the present invention.

FIG. 16 is a perspective view of a distal end part of a distal end portion of the insertion section including a stereo camera. Two observation windows 11a and 11b and two illumination windows 11c are disposed on a distal end face of the distal end portion 11. An image pickup optical system and an image pickup device are disposed on a rear side of the respective observation windows 11a and 11b. The image pickup optical system and the image pickup device configure image pickup units 11d. Two image pickup units 11d configure the stereo camera.

Positions of respective points of the inner wall of the large intestine can be calculated by the triangulation from positions of stereo matching regions in two endoscopic images acquired by the stereo camera disposed at the distal end portion 11.

Figure 17:
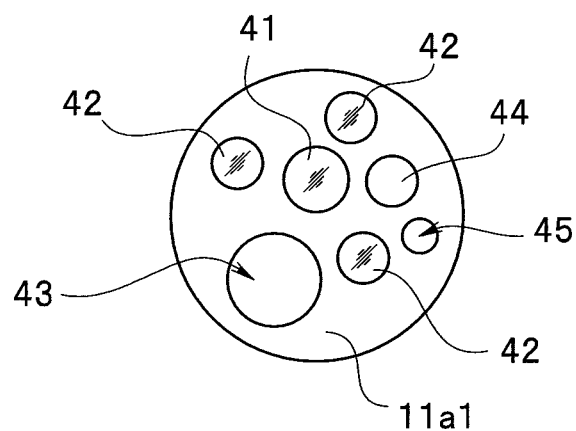
FIG. 17 is a plan view of a distal end face of the distal end portion of the insertion section including a plurality of illumination windows according to the embodiment of the present invention.

3. When Positions of Feature Points are Calculated Using an Illuminance Difference Stereo Image A method of calculating positions of respective feature points using an illuminance difference stereo image is explained. FIG. 17 is a plan view of a distal end face of a distal end portion of an insertion section including a plurality of illumination windows. FIG. 17 is a view of a distal end face 11a1 of the distal end portion 11 viewed from a distal end side of the insertion section 2b.

As shown in FIG. 17, an observation window 41, three illumination windows 42, a forceps port 43, a cleaning nozzle 44, and a sub water feeding port 45 are provided on the distal end face 11a1 of the distal end portion 11. The image pickup units 11d are provided on a rear side of the observation window 41. The three illumination windows 42 are disposed around the observation window 41. A distal end face of a not-shown light guide is disposed on a rear side of the respective illumination windows 42. The forceps port 43 is an opening from which a treatment instrument inserted through a treatment instrument insertion channel provided in the insertion section 2b projects. The cleaning nozzle 44 discharges water for cleaning a surface of the observation window 41. The sub water feeding port 45 is an opening from which water for sub water feeding is discharged.

Driving of a plurality of light emitting diodes for illumination provided in the light source apparatus 4 is controlled, whereby three illumination lights emitted from the three illumination windows 42 can be switched and selectively emitted.

A state of a shadow portion in an image on a surface of an object changes according to the switching of the illumination lights. Accordingly, a distance to the shadow portion on the surface of the object can be calculated based on an amount of the change. In other words, a three-dimensional structure of the lumen can be determined based on an illuminance difference stereo image from an image of a shadow region in a picked-up image obtained by illuminating the object with a plurality of illumination units that are selectively caused to operate.

4. When a Luminal Structure is Calculated Using a Distance Sensor

A method of calculating positions of respective points on the inner wall of the lumen using a distance sensor provided in the distal end portion 11 is explained.

Figure 18:
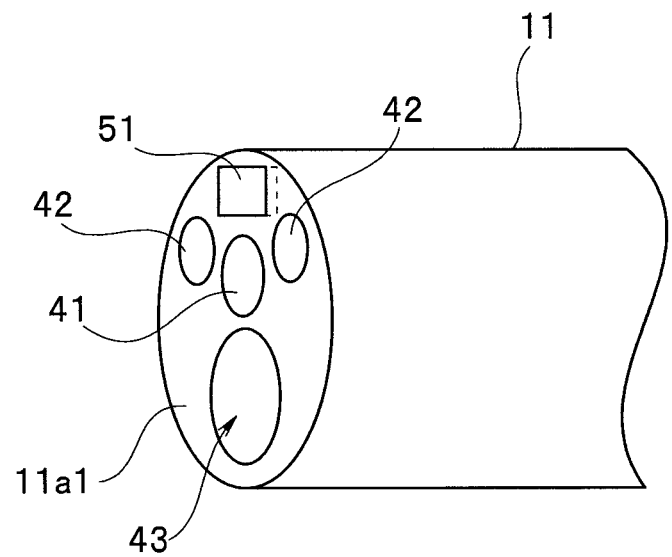
FIG. 18 is a perspective view of a distal end part of the distal end portion of an insertion section including a distance sensor according to the embodiment of the present invention.

FIG. 18 is a perspective view of a distal end part of a distal end portion of an insertion section including a distance sensor. The observation window 41, the two illumination windows 42, the forceps port 43, and a distance sensor 51 are disposed on the distal end face 11a1 of the distal end portion 11.

The distance sensor 51 is a TOF (time of flight) sensor and, here, is a sensor that detects a distance image with TOF. The distance sensor 51 measures a flight time of light to thereby measure a distance. A TOF function is embedded in respective pixels of an image sensor. Accordingly, the distance sensor 51 obtains distance information for each of the pixels. In other words, the distance sensor 51 is provided at the distal end portion 11 of the insertion section 2b and detects a distance from the distal end portion 11 to the inner wall of the lumen.

Position information of respective points of the inner wall of the large intestine, that is, a three-dimensional structure of the lumen can be calculated from distances about the respective pixels detected by the distance sensor 51 and a position and a posture, that is, disposition of the distal end portion 11. Note that the distance sensor may be a sensor of another scheme such as LiDAR (light detection and ranging/laser imaging detection and ranging).

Figure 19:
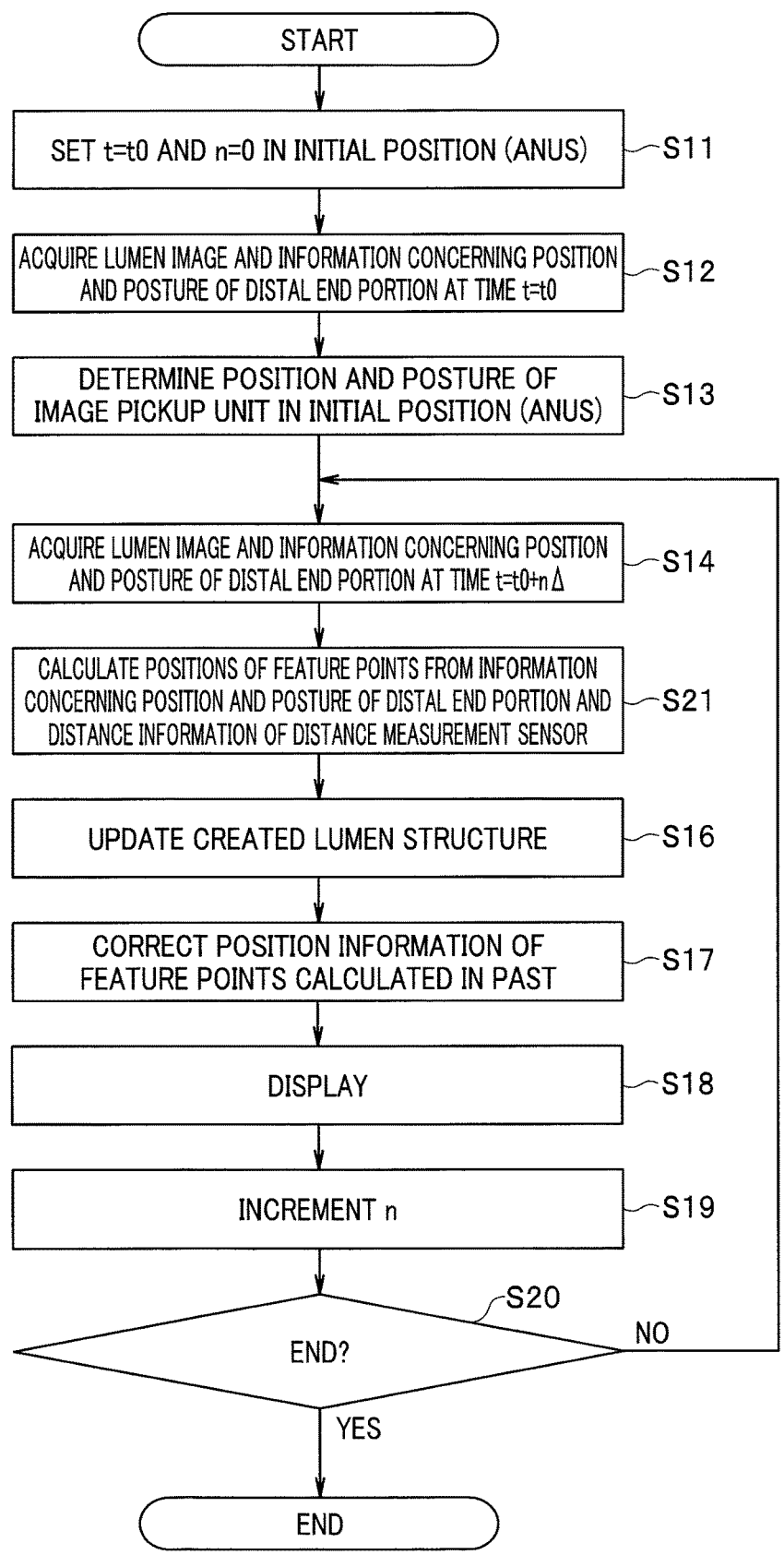
FIG. 19 is a flowchart of a method of performing calculation of a three-dimensional position of an inner wall of a lumen using the distance sensor according to the embodiment of the present invention.

FIG. 19 is a flowchart of a method of calculating a three-dimensional position of the inner wall of the lumen using the distance sensor. In FIG. 19, the same processing as the processing shown in FIG. 13 is denoted by the same step numbers and explanation of the processing is omitted. Only different processing is explained.

When the distance sensor 51 is used, by setting one or more predetermined pixels of the distance sensor 51 as feature points, three-dimensional positions of respective points of the inner wall of the large intestine can be calculated from distance information of the respective pixels of the distance sensor 51 and information concerning a position and a posture of the distal end portion 11. A luminal structure is configured by a set of three-dimensional position information of the respective points of the inner wall. In other words, in FIG. 13, in S21, the processor 21 calculates a three-dimensional coordinate of a point (a feature point), a distance of which is measured, from distance information outputted from the distance sensor 51 and the information concerning the position and the posture of the distal end portion 11 obtained in S14.

5. Distance Measurement by Another Method

Note that an illumination unit that emits predetermined pattern light may be provided in the distal end portion 11.

Distance measurement from the distal end portion 11 to the inner wall may be performed by pattern light projection.

As explained above, according to the embodiment explained above, structure information of the inner wall of the large intestine can be obtained using information concerning a position and a posture (that is, disposition) of the distal end portion 11 of the insertion section 2b and image information of an endoscopic image or distance information of the distance sensor.

In the embodiment explained above, since information concerning a position and a posture of the distal end portion 11 is obtained, even when an endoscopic image is not obtained or distance information of the distance sensor 51 is not obtained because the distal end portion is too close to a luminal wall, although a structure of a lumen portion where an endoscopic image and the like are not obtained cannot be calculated, a structure of a lumen portion where an endoscopic image and the like are obtained can be calculated.

Figure 20:
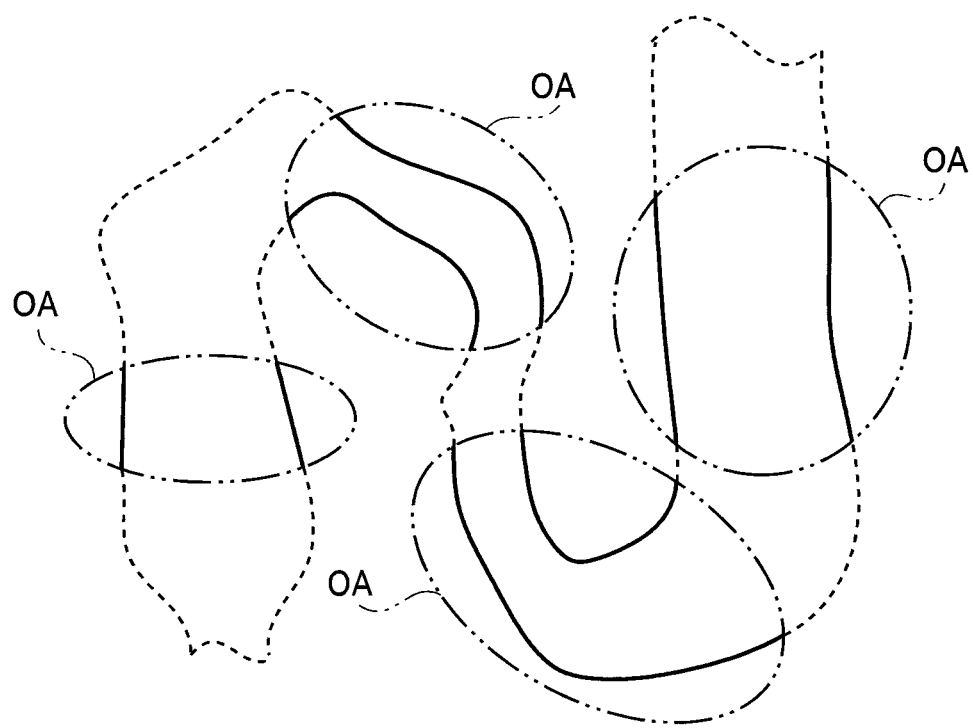
FIG. 20 is a diagram for explaining an example of a partially calculated luminal structure according to the embodiment of the present invention.

FIG. 20 is a diagram for explaining an example of a partially calculated luminal structure. In FIG. 20, portions indicated by ellipse of alternate long and two short dashes lines indicate partial regions of the large intestine where endoscopic images are obtained or distance information of the distance sensor 51 is obtained. About portions indicated by dotted lines, although endoscopic images are not obtained or distance information of the distance sensor 51 is not obtained, structure information of partial regions indicated by solid lines is calculated. In other words, in respective sets, when overlap of feature points with other sets is absent or cannot be determined, a plurality of luminal structures without connection are disposed in respective positions based on position information of the respective luminal structures.

Accordingly, even if an endoscopic image is not obtained halfway, positions of respective feature points can be calculated from a plurality of endoscopic images. Therefore, as a result, a three-dimensional model structure of the lumen can be partially calculated.

Note that, in the embodiment explained above, the magnetic sensor 16 is used as a position sensor for detecting a position and a posture of the distal end portion 11 of the insertion section 2b. However, the position and the posture of the distal end portion 11 may be detected by another means.

Figure 21:
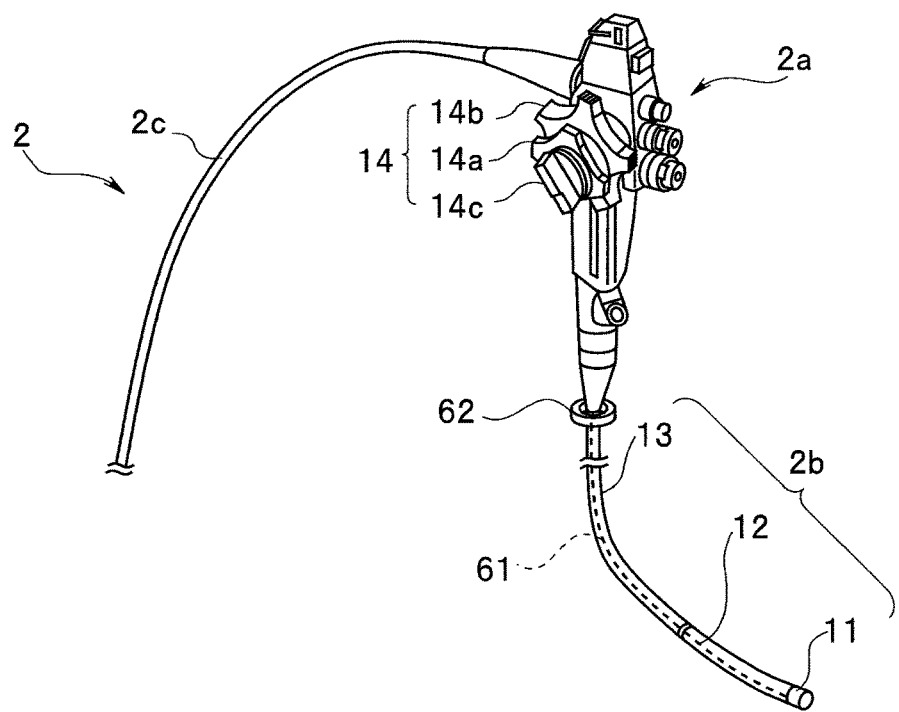
FIG. 21 is a diagram for explaining a method of detecting a position and a posture of the distal end portion using an endoscope including a shape sensor and a sensor that detects an insertion amount and a twist amount according to the embodiment of the present invention.

FIG. 21 is a diagram for explaining a method of detecting a position and a posture of the distal end portion 11 using an endoscope including a shape sensor and a sensor that detects an insertion amount and a twist amount.

A shape sensor 61 is disposed from a proximal end to a distal end on an inside of the insertion section 2b. The shape sensor 61 is, for example, a fiber sensor, which is a bending sensor that detects a bending amount from a curvature of a specific part using an optical fiber.

An insertion amount/twist amount sensor 62 is disposed near the anus and has a cylindrical shape having a hole through which the insertion section 2b can be inserted. An encoder for detecting an insertion amount in an axial direction of the insertion section 2b and an encoder that detects a rotation amount around an axis of the insertion section 2b are disposed on an inner circumferential surface of the hole of the insertion amount/twist amount sensor 62. Accordingly, it is possible to estimate a position and a posture of the distal end portion 11, with a position of the anus set as a reference, based on an insertion amount and a twist amount of the insertion section 2b using the shape sensor 61 and the insertion amount/twist amount sensor 62.

Figure 22:
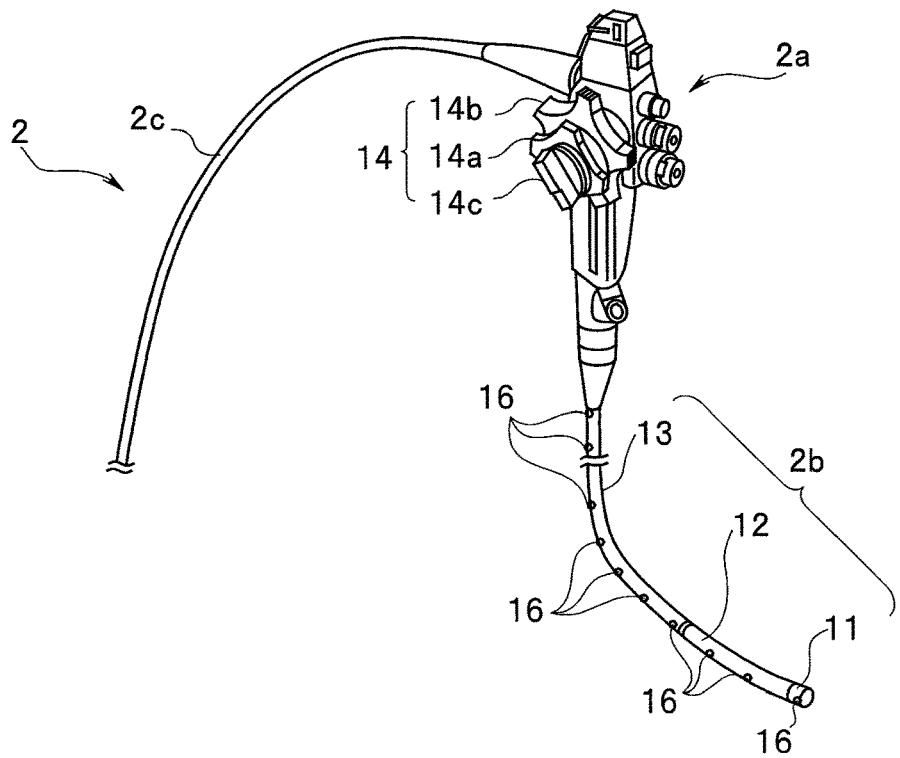
FIG. 22 is a perspective view of an endoscope in which a plurality of magnetic sensors are disposed in the insertion section according to the embodiment of the present invention.

The shape sensor 61 may not be a sensor that makes use of an optical fiber. A shape of the insertion section 2b may be detected by providing one magnetic sensor 16 at the distal end portion 11 and disposing a plurality of magnetic sensors 16 at a predetermined interval in the insertion section 2b. FIG. 22 is a perspective view of an endoscope in which the plurality of magnetic sensors 16 are disposed in the insertion section 2b. The shape of the insertion section 2b can be calculated from position information of the plurality of magnetic sensors 16 shown in FIG. 22.

Note that, as indicated by a dotted line in FIG. 2, the shape sensor 61 explained above may be disposed in the insertion section 2b of the endoscope 2. If the shape sensor 61 is used, an overall shape of the insertion section 2b can also be grasped.

In the embodiment explained above, the doctor calculates a luminal structure while viewing an endoscopic image. However, when a hidden portion such as a rear side of a wrinkle is present, a luminal structure of a region of the hidden portion is not calculated. The hidden portion is a region not reflected in the endoscopic image. In the region not included in the endoscopic image, a luminal structure is not generated. Therefore, presence of the hidden portion may be detected from the endoscopic image or the like and notified to the doctor.

Figure 23:
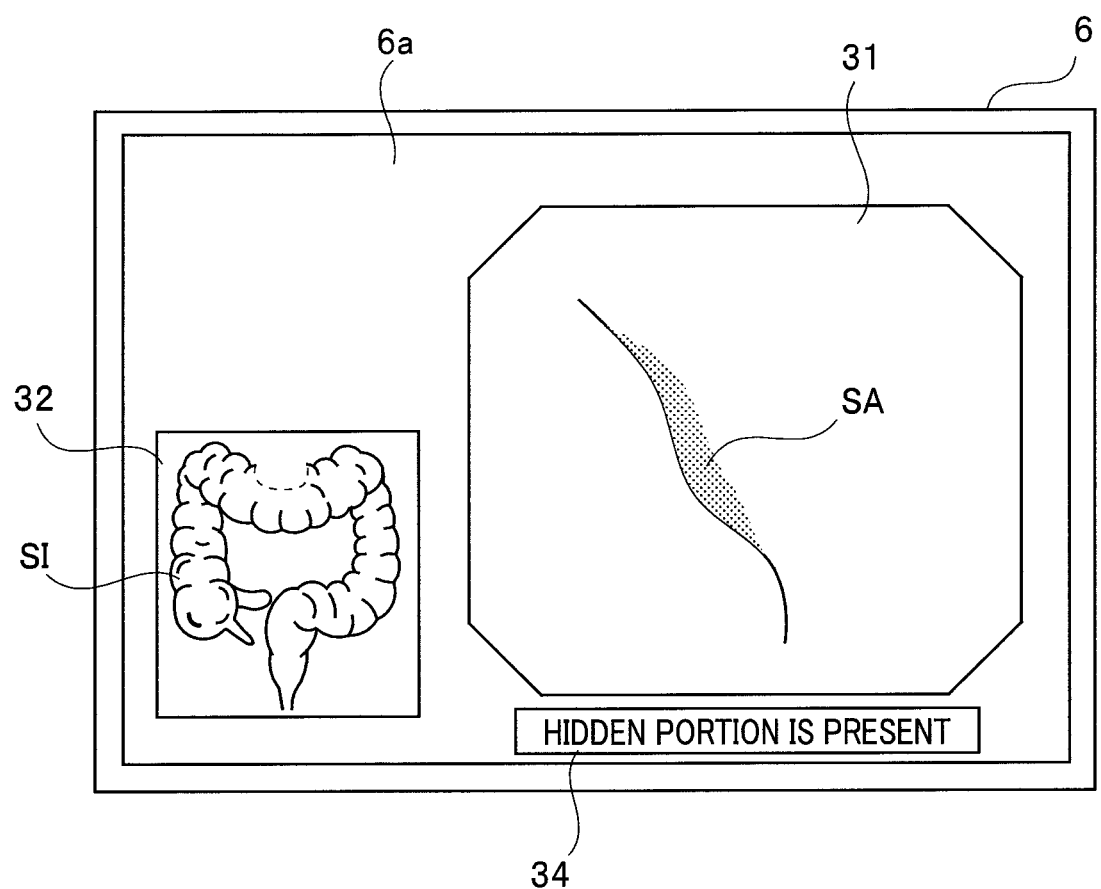
FIG. 23 is a diagram showing a display example of the monitor at a time when a hidden portion is present according to the embodiment of the present invention.

FIG. 23 is a diagram showing a display example of the monitor 6 at a time when a hidden portion is present. An endoscopic image of the large intestine in which a shadow is formed on a depth side in a part of the inner wall is displayed in the endoscopic image display region 31 of the display screen 6a of the monitor 6. In a portion SA of a dark shadow not irradiated with illumination light, brightness decreases stepwise compared with other portions. Accordingly, when a luminance difference is equal to or larger than a predetermined luminance value between pixels adjacent to each other or pixel regions adjacent to each other, it can be determined that a hidden portion is present.

In such a case, by causing the monitor 6 to display a predetermined message like a popup window 34 shown in FIG. 23, it is possible to notify the user and cause the user to observe the hidden portion. A recess such as a diverticulum is also included in the hidden portion. When the user views the predetermined message and observes the hidden portion, information concerning a luminal structure in the observed region is calculated.

Note that, in the example explained above, the hidden portion is detected according to presence or absence of the shadow region not irradiated with illumination light. However, presence or absence of the same hidden portion may be detected using the distance image information of the distance sensor 51 or the like explained above. For example, when a distance difference is equal to or larger than a predetermined distance value between pixels adjacent to each other or pixel regions adjacent to each other, it can be determined that a hidden portion is present.

Figure 24:
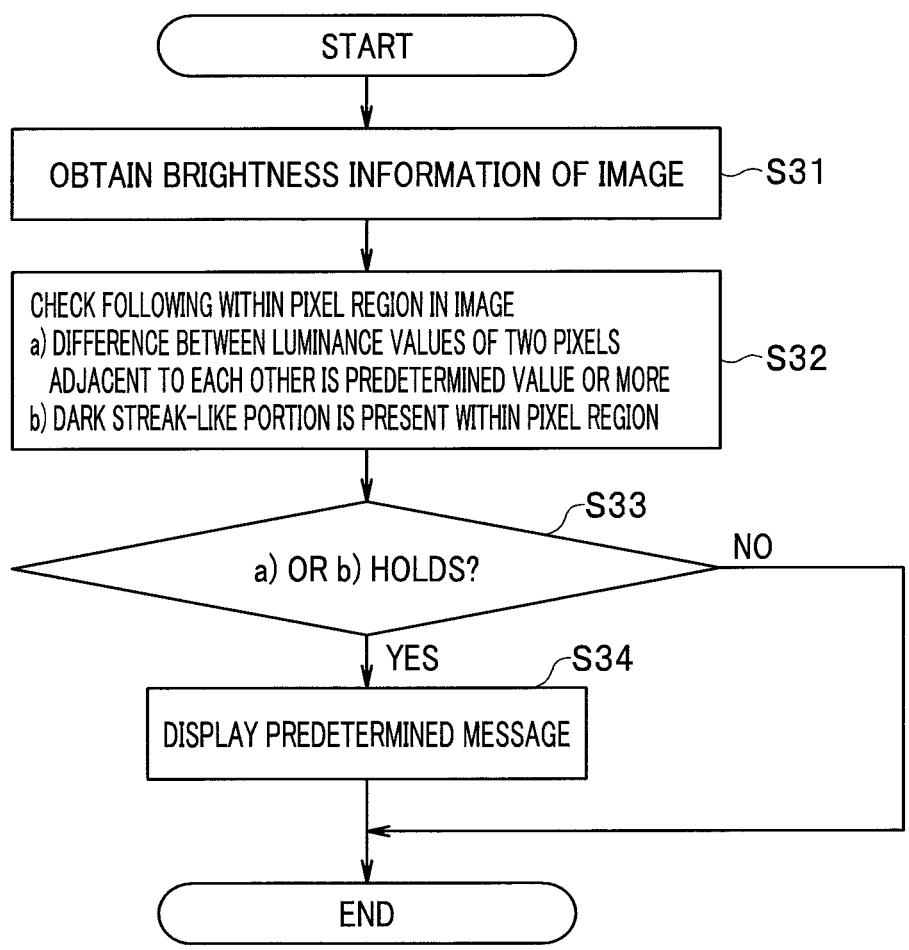
FIG. 24 is a flowchart showing an example of a flow of notification processing for an unobserved region by a luminance value of an image according to the embodiment of the present invention.

FIG. 24 is a flowchart showing an example of a flow of notification processing for an unobserved region by a luminance value of an image. The processing in FIG. 24 is executed in parallel to the processing shown in FIG. 4 when an endoscopic image at a new visual point is acquired in S2 in FIG. 4. The processor 21 obtains brightness information of the endoscopic image at the new visual point acquired in S2 (S31). In other words, luminance information of respective pixels in the image is acquired.

The processor 21 determines, that is, checks a) whether a difference between luminance values of two pixels adjacent to each other is equal to or larger than a predetermined value or b) whether a dark streak portion is present in a predetermined pixel region in the image (S32).

The processor 21 determines whether a) or b) holds (S33). When a) or b) holds (S33: YES), the processor 21 determines that a hidden portion is likely to be present in a visual field and displays a predetermined message on the monitor 6 (S34). The predetermined message is, for example, a message like the popup window 34 shown in FIG. 23. When neither a) nor b) holds (S33: NO), the processor 21 does no processing. Processing in S34 configures a notifying unit that performs predetermined notification when a difference of a luminance value between two pixels adjacent to each other or two pixel regions adjacent to each other in a picked-up image is equal to or larger than a predetermined value.

FIG. 25 is a flowchart showing an example of a flow of notification processing for an unobserved region by a distance image of the distance sensor 51. Processing shown in FIG. 25 is executed in parallel to the processing shown in FIG. 4 when an endoscopic image at a new visual point is acquired in S2 in FIG. 4. The processor 21 obtains distance image information of the distance sensor 51 at the new visual point acquired in S2 (S41). In other words, distance information of respective pixels in the image is acquired.

The processor 21 determines, that is, checks c) whether a difference between distances of two pixels adjacent to each other is equal to or larger than a predetermined value or d) whether a portion where a change in a distance does not continue is present in a predetermined pixel region in the image (S42).

The processor 21 determines whether c) or d) holds (S43). When c) or d) holds (S43: YES), the processor 21 determines that a hidden portion is likely to be present in a visual field and displays a predetermined message on the monitor 6 (S44). The predetermined message is, for example, a message like the popup window 34 shown in FIG. 23. When neither c) nor d) holds (S43: NO), the processor 21 does no processing. Processing in S43 configures a notifying unit that performs predetermined notification when a difference of a distance value between two pixels adjacent to each other or two pixel regions adjacent to each other in a distance image is equal to or larger than a predetermined value.

The present invention is not limited to the embodiment explained above. Various changes, alterations, and the like are possible within a range in which the gist of the present invention is not changed.

What is claimed is:

1. A luminal structure calculation apparatus comprising:
at least one processor including hardware, wherein the at least one processor is configured to:
acquire picked-up images at a plurality of points in time including a plurality of feature points that are a same site of an object acquired by an image sensor provided in an insertion section inserted into a lumen serving as the object and three-dimensional disposition including information concerning at least a part of a position or a direction of the image sensor,
calculate a plurality of partial three-dimensional structures, which are parts of a three-dimensional structure of the lumen, including information concerning positions of the feature points based on the picked-up images at the plurality of points in time and the three-dimensional disposition,
determine, based on the three-dimensional disposition at a time when the respective partial three-dimensional structures are created, disposition of the plurality of partial three-dimensional structures, and correct the disposition of the partial three-dimensional structures based on positions of the feature points common to the plurality of partial three-dimensional structures to calculate the three-dimensional structure of the lumen,
wherein the lumen includes a fixed portion fixed from an outside and a movable portion not fixed from the outside, and
when the feature points similar among the plurality of partial three-dimensional structures are extracted, the at least one processor is further configured to compare a difference between distances from the similar feature points to the fixed portion with a predetermined reference value to determine whether the similar feature points are the feature points common to the plurality of partial three-dimensional structures.

2. The luminal structure calculation apparatus according to claim 1, wherein the at least one processor is configured to:
extract the plurality of feature points in the respective picked-up images,
calculate positions in a three-dimensional space of the respective feature points from positions on the picked-up images of the plurality of feature points and the three-dimensional disposition of the insertion section, and
calculate the three-dimensional structure of the lumen from the calculated positions of the respective feature points in the three-dimensional space.

3. The luminal structure calculation apparatus according to claim 2, wherein the at least one processor is configured to:
extract the plurality of feature points reflected in common in the picked-up images at the plurality of points in time,
acquire the three-dimensional disposition information of the insertion section at the plurality of points in time, and
calculate a position in the three-dimensional space of the plurality of feature points based on the three-dimensional disposition information of the insertion section at the plurality of points in time and positions on the picked-up images of the plurality of feature points reflected in common in the picked-up images at the plurality of points in time.

4. The luminal structure calculation apparatus according to claim 1, wherein
the at least one processor is configured to calculate a distance between the partial three-dimensional structure corresponding to the movable portion and the fixed portion and correct the disposition of the partial three-dimensional structures based on the distance between the partial three-dimensional structure and the fixed portion.

5. The luminal structure calculation apparatus according to claim 2, wherein the at least one processor is configured to determine positions in the three-dimensional space of the respective feature points with error adjustment.

6. The luminal structure calculation apparatus according to claim 5, wherein the at least one processor is configured to regard the disposition detected by a detection apparatus as known and determine the positions in the three-dimensional space of the respective feature points with the error adjustment by bundle adjustment.

7. The luminal structure calculation apparatus according to claim 2, wherein the at least one processor is configured to calculate a position in the three-dimensional space of the feature point based on triangulation from the three-dimensional disposition information of the insertion section at the plurality of points in time and a position on the picked-up images of the feature points reflected in common in the picked-up images at the plurality of points in time.

8. The luminal structure calculation apparatus according to claim 1, wherein the at least one processor is configured to determine a three-dimensional structure of the lumen based on an illuminance difference stereo image from an image in a shadow region in the picked-up images at the plurality of points in time including the same site of the object obtained by switching an illumination unit caused to emit illumination light in a plurality of illumination units provided at the distal end portion.

9. The luminal structure calculation apparatus according to claim 1, wherein the at least one processor is configured to determine, using a predetermined extension and contraction ratio upper limit value of respective feature points set for each region of the lumen, whether common feature points reflected in the picked-up images in plurality are same.

10. The luminal structure calculation apparatus according to claim 9, wherein, when a change amount of a position of a detected feature point is equal to or smaller than the predetermined extension and contraction ratio upper limit value, the at least one processor is configured to determine that the respective feature points reflected in the respective picked-up images are the same.

11. The luminal structure calculation apparatus according to claim 1, wherein the at least one processor is configured to perform predetermined notification when a difference of a luminance value between two pixels or two pixel regions adjacent to each other in the picked-up images is equal to or larger than a predetermined value.

12. A creation method for luminal structure information comprising:
  acquiring picked-up images of an object at a plurality of points in time including a plurality of feature points that are a same site of the object acquired by an image sensor provided in an insertion section inserted into a lumen serving as the object;
  acquiring three-dimensional disposition including information concerning at least one of a position or a direction of the insertion section;
  calculating a plurality of partial three-dimensional structures, which are parts of a three-dimensional structure of the lumen, including information concerning positions a of the feature points based on the picked-up images at the plurality of points in time and the three-dimensional disposition,
  determining, based on the three-dimensional disposition at a time when the respective partial three-dimensional structures are created, disposition of the plurality of partial three-dimensional structures,
  correcting the disposition of the partial three-dimensional structures based on positions of the feature points common to the plurality of partial three-dimensional structures to calculate the three-dimensional structure of the lumen, and
  when the feature points similar among the plurality of partial three-dimensional structures are extracted, comparing a difference between distances from the similar feature points to the fixed portion with a predetermined reference value to determine whether the similar feature points are the feature points common to the plurality of partial three-dimensional structures.

13. A non-transitory recording medium recording a luminal structure information creation program, the luminal structure information creation program causing a computer to execute:
  processing for acquiring picked-up images of an object at a plurality of points in time including a plurality of feature points that are a same site of the object acquired by an image sensor provided in an insertion section inserted into a lumen serving as the object;
  processing for detecting three-dimensional disposition including information concerning at least one of a position or a direction of the insertion section;
  processing for calculating a plurality of partial three-dimensional structures, which are parts of a three-dimensional structure of the lumen, including information concerning positions of the feature points based on the picked-up images at the plurality of points in time and the three-dimensional disposition,
  processing for determining, based on the three-dimensional disposition at a time when the respective partial three-dimensional structures are created, disposition of the plurality of partial three-dimensional structures,
  processing for correcting the disposition of the partial three-dimensional structures based on positions of the feature points common to the plurality of partial three-dimensional structures to calculate the three-dimensional structure of the lumen, and
  processing for, when the feature points similar among the plurality of partial three-dimensional structures are extracted, comparing a difference between distances from the similar feature points to the fixed portion with a predetermined reference value to determine whether the similar feature points are the feature points common to the plurality of partial three-dimensional structures.

* * * * *